(12) United States Patent
Gardiner et al.

(10) Patent No.: US 7,547,313 B2
(45) Date of Patent: Jun. 16, 2009

(54) TISSUE CONNECTOR APPARATUS AND METHODS

(75) Inventors: Barry Gardiner, Orinda, CA (US); Laurent Schaller, Los Altos, CA (US); Isidro Matias Gandionco, Fremont, CA (US); John Nguyen, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 645 days.

(21) Appl. No.: 10/439,973

(22) Filed: May 16, 2003

(65) Prior Publication Data
US 2003/0195531 A1  Oct. 16, 2003

Related U.S. Application Data

(63) Continuation of application No. 09/089,884, filed on Jun. 3, 1998, now Pat. No. 6,607,541.

(51) Int. Cl.
*A61B 17/08* (2006.01)
(52) U.S. Cl. .................... 606/153; 606/151
(58) Field of Classification Search ............ 606/153, 606/151, 142, 144, 148, 213, 215–217, 219, 606/157, 158, 222; 128/898; 227/66, 67
See application file for complete search history.

(56) References Cited

U.S. PATENT DOCUMENTS

| 43,098 | A | 6/1864 | Cooper |
|---|---|---|---|
| 636,728 | A | 11/1899 | Kindel |
| 655,190 | A | 8/1900 | Bramson |
| 1,087,186 | A | 2/1914 | Scholfield |
| 1,167,014 | A | 1/1916 | O'Brien |
| 1,539,221 | A | 5/1925 | John |
| 1,583,271 | A | 5/1926 | Biro |
| 1,625,602 | A | 4/1927 | Gould et al. |
| 1,867,624 | A | 7/1932 | Hoffman |
| 2,201,610 | A | 5/1940 | Dawson |
| 2,240,330 | A | 4/1941 | Flagg et al. |
| 2,256,382 | A | 9/1941 | Dole |
| 2,264,679 | A | 12/1941 | Ravel |

(Continued)

FOREIGN PATENT DOCUMENTS

DE  219 999  3/1910

(Continued)

OTHER PUBLICATIONS

"VSC Clip Applier System," (1995). Auto Suture Company, a Division of U.S. Surgical Corporation, Norwalk, Connecticut, 8 pages.

(Continued)

*Primary Examiner*—Julian W Woo
(74) *Attorney, Agent, or Firm*—Mike Jaro; Jeff Hohenshell

(57) ABSTRACT

A tissue connector assembly having a flexible member and a surgical clip releasably coupled to the flexible member. A needle may be secured to one end portion of the flexible member with the surgical clip coupled to the other end portion of the flexible member. A locking device may be used to couple the flexible member to the surgical clip. A method for connecting tissues is also disclosed. The method includes drawing tissue portions together with a clip assembly and securing the tissue portions together with the clip assembly.

22 Claims, 11 Drawing Sheets

U.S. PATENT DOCUMENTS

| | | | |
|---|---|---|---|
| 2,413,142 A | 12/1946 | Jones et al. | |
| 2,430,293 A | 11/1947 | Howells | |
| 2,505,358 A | 4/1950 | Gusberg et al. | |
| 2,516,710 A | 7/1950 | Mascolo | |
| 2,715,486 A | 8/1955 | Marcoff-Moghadam et al. | |
| 2,890,519 A | 6/1959 | Storz, Jr. | |
| 2,940,452 A | 6/1960 | Smialowski | |
| 3,055,689 A | 9/1962 | Jorgensen | |
| 3,057,355 A | 10/1962 | Smialowski | |
| 3,082,426 A | 3/1963 | Miles | |
| 3,143,742 A | 8/1964 | Cromie | |
| 3,150,379 A | 9/1964 | Brown | |
| 3,180,337 A | 4/1965 | Smialowski | |
| 3,249,104 A | 5/1966 | Hohnstein | |
| 3,274,658 A | 9/1966 | Pile | |
| 3,452,742 A | 7/1969 | Muller | |
| 3,506,012 A | 4/1970 | Brown | |
| 3,509,882 A | 5/1970 | Blake | |
| 3,547,103 A | 12/1970 | Cook | |
| 3,570,497 A | 3/1971 | Lemole | |
| 3,608,095 A | 9/1971 | Barry | |
| 3,638,654 A | 2/1972 | Akuba | |
| 3,656,185 A | 4/1972 | Carpentier | |
| RE27,391 E | 6/1972 | Merser | |
| 3,753,438 A | 8/1973 | Wood et al. | |
| 3,776,237 A | 12/1973 | Hill et al. | |
| 3,802,438 A | 4/1974 | Wolvek | |
| 3,825,009 A | 7/1974 | Williams | |
| 3,837,345 A | 9/1974 | Matar | |
| 3,874,388 A | 4/1975 | King et al. | |
| 3,875,648 A | 4/1975 | Bone | |
| 3,905,403 A | 9/1975 | Smith et al. | |
| 3,908,662 A | 9/1975 | Razgulov et al. | |
| 3,910,281 A | 10/1975 | Kletschka et al. | |
| 3,958,576 A | 5/1976 | Komiya | |
| 3,976,079 A | 8/1976 | Samuels | |
| 3,995,619 A | 12/1976 | Glatzer | |
| 4,006,747 A | 2/1977 | Kronenthal et al. | |
| 4,018,228 A | 4/1977 | Goosen | |
| 4,038,725 A | 8/1977 | Keefe | |
| 4,042,979 A | 8/1977 | Angell | |
| 4,073,179 A | 2/1978 | Hickey et al. | |
| 4,103,690 A | 8/1978 | Harris | |
| 4,111,206 A | 9/1978 | Vishnevsky et al. | |
| 4,129,059 A | 12/1978 | Van Eck | |
| 4,140,125 A | 2/1979 | Smith | |
| 4,170,990 A | 10/1979 | Baumgart et al. | |
| 4,185,636 A | 1/1980 | Gabbay et al. | |
| 4,192,315 A | 3/1980 | Hilzinger et al. | |
| 4,214,587 A | 7/1980 | Sakura | |
| 4,217,902 A | 8/1980 | March | |
| 4,243,048 A | 1/1981 | Griffin | |
| 4,324,248 A | 4/1982 | Perlin | |
| 4,345,601 A | 8/1982 | Fukuda | |
| 4,352,358 A | 10/1982 | Angelchik | |
| 4,366,819 A | 1/1983 | Kaster | |
| 4,396,139 A | 8/1983 | Hall et al. | |
| 4,416,266 A | 11/1983 | Baucom | |
| 4,456,017 A | 6/1984 | Miles | |
| 4,465,071 A | 8/1984 | Samuels et al. | |
| 4,470,415 A | 9/1984 | Wozniak | |
| 4,470,533 A | 9/1984 | Schuler | |
| 4,474,181 A | 10/1984 | Schenck | |
| 4,485,816 A | 12/1984 | Krumme | |
| 4,492,229 A | 1/1985 | Grunwald | |
| 4,522,207 A | 6/1985 | Klieman et al. | |
| 4,523,592 A | 6/1985 | Daniel | |
| 4,532,927 A | 8/1985 | Miksza | |
| 4,535,764 A | 8/1985 | Ebert | |
| 4,549,545 A | 10/1985 | Levy | |
| 4,553,542 A | 11/1985 | Schenck et al. | |
| 4,576,605 A | 3/1986 | Kaidash et al. | |
| 4,586,502 A | 5/1986 | Bedi et al. | |
| 4,586,503 A | 5/1986 | Kirsch et al. | |
| 4,593,693 A | 6/1986 | Schenck | |
| 4,595,007 A | 6/1986 | Mericle | |
| 4,612,932 A | 9/1986 | Caspar et al. | |
| 4,622,970 A | 11/1986 | Wozniak | |
| 4,624,255 A | 11/1986 | Schenck et al. | |
| 4,637,380 A | 1/1987 | Orejola | |
| 4,641,652 A | 2/1987 | Hutterer et al. | |
| 4,665,906 A | 5/1987 | Jervis | |
| 4,665,917 A | 5/1987 | Clanton et al. | |
| 4,683,895 A | 8/1987 | Pohndorf | |
| 4,706,362 A | 11/1987 | Strausburg | |
| 4,719,917 A | 1/1988 | Barrows et al. | |
| 4,719,924 A | 1/1988 | Crittenden et al. | |
| 4,730,615 A | 3/1988 | Sutherland et al. | |
| 4,732,151 A | 3/1988 | Jones | |
| 4,809,695 A | 3/1989 | Gwathmey et al. | |
| 4,820,298 A | 4/1989 | Leveen et al. | |
| 4,844,318 A | 7/1989 | Kunreuther | |
| 4,873,975 A | 10/1989 | Walsh et al. | |
| 4,890,615 A | 1/1990 | Caspari et al. | |
| 4,896,668 A | 1/1990 | Popoff et al. | |
| 4,899,744 A | 2/1990 | Fujitsuka et al. | |
| 4,901,721 A | 2/1990 | Hakki | |
| 4,923,461 A | 5/1990 | Caspari et al. | |
| 4,924,866 A | 5/1990 | Yoon | |
| 4,926,860 A | 5/1990 | Stice et al. | |
| 4,929,240 A | 5/1990 | Kirsch et al. | |
| 4,930,674 A | 6/1990 | Barak | |
| 4,932,955 A | 6/1990 | Merz et al. | |
| 4,935,027 A | 6/1990 | Yoon | |
| 4,950,015 A | 8/1990 | Nejib et al. | |
| 4,950,283 A | 8/1990 | Dzubow et al. | |
| 4,950,285 A | 8/1990 | Wilk | |
| 4,957,498 A | 9/1990 | Caspari et al. | |
| 4,983,176 A | 1/1991 | Cushman et al. | |
| 4,990,152 A | 2/1991 | Yoon | |
| 4,991,567 A | 2/1991 | McCuen et al. | |
| 4,994,069 A | 2/1991 | Ritchart et al. | |
| 4,997,439 A | 3/1991 | Chen | |
| 5,002,550 A | 3/1991 | Li | |
| 5,002,562 A | 3/1991 | Oberlander | |
| 5,002,563 A | 3/1991 | Pyka et al. | |
| 5,007,920 A | 4/1991 | Torre | |
| 5,011,481 A | 4/1991 | Myers et al. | |
| 5,020,713 A | 6/1991 | Kunreuther | |
| 5,026,379 A | 6/1991 | Yoon | |
| 5,032,127 A | 7/1991 | Frazee et al. | |
| 5,035,692 A | 7/1991 | Lyon et al. | |
| 5,035,702 A | 7/1991 | Taheri | |
| 5,037,433 A * | 8/1991 | Wilk et al. | 606/222 |
| 5,042,707 A | 8/1991 | Taheri | |
| 5,047,047 A | 9/1991 | Yoon | |
| 5,053,047 A | 10/1991 | Yoon | |
| 5,064,431 A | 11/1991 | Gilbertson et al. | |
| 5,074,874 A | 12/1991 | Yoon, Inbae et al. | |
| 5,088,692 A | 2/1992 | Weiler | |
| 5,100,418 A | 3/1992 | Yoon et al. | |
| 5,100,421 A | 3/1992 | Christoudias | |
| 5,104,407 A | 4/1992 | Lam et al. | |
| 5,119,983 A | 6/1992 | Green et al. | |
| 5,123,913 A | 6/1992 | Wilk et al. | |
| 5,127,413 A | 7/1992 | Ebert | |
| 5,152,769 A | 10/1992 | Baber | |
| 5,154,189 A | 10/1992 | Oberlander | |
| 5,158,566 A | 10/1992 | Pianetti | |
| 5,171,250 A | 12/1992 | Yoon | |
| 5,171,252 A | 12/1992 | Friedland | |
| 5,174,087 A | 12/1992 | Bruno | |
| 5,178,634 A | 1/1993 | Ramos Martinez | |
| 5,192,294 A | 3/1993 | Blake | |

| | | | | | |
|---|---|---|---|---|---|
| 5,196,022 A | 3/1993 | Bilweis | 5,527,342 A | 6/1996 | Pietrzak et al. |
| 5,201,880 A | 4/1993 | Wright et al. | 5,533,236 A | 7/1996 | Tseng |
| 5,207,694 A | 5/1993 | Broome | 5,538,509 A | 7/1996 | Dunlap et al. |
| 5,217,027 A | 6/1993 | Hermens | 5,545,214 A | 8/1996 | Stevens |
| 5,219,358 A | 6/1993 | Bendel et al. | 5,549,619 A | 8/1996 | Peters et al. |
| 5,221,259 A | 6/1993 | Weldon et al. | 5,556,411 A | 9/1996 | Taoda et al. |
| 5,222,961 A | 6/1993 | Nakao et al. | 5,562,685 A | 10/1996 | Mollenauer et al. |
| 5,222,976 A | 6/1993 | Yoon | 5,569,205 A | 10/1996 | Hart et al. |
| 5,234,447 A | 8/1993 | Kaster et al. | 5,569,274 A | 10/1996 | Rapacki et al. |
| 5,236,440 A | 8/1993 | Hlavacek | 5,569,301 A | 10/1996 | Granger et al. |
| 5,242,456 A | 9/1993 | Nash et al. | 5,571,119 A | 11/1996 | Atala |
| 5,242,457 A | 9/1993 | Akopov et al. | 5,571,175 A | 11/1996 | Vanney et al. |
| 5,246,443 A | 9/1993 | Mai | 5,582,616 A | 12/1996 | Bolduc et al. |
| 5,250,053 A | 10/1993 | Snyder | 5,582,619 A | 12/1996 | Ken |
| 5,258,011 A | 11/1993 | Drews | 5,584,879 A | 12/1996 | Reimold et al. |
| 5,261,917 A | 11/1993 | Hasson et al. | 5,586,983 A | 12/1996 | Sanders et al. |
| 5,269,783 A | 12/1993 | Sander | 5,591,179 A | 1/1997 | Edelstein |
| 5,269,809 A | 12/1993 | Hayhurst et al. | 5,593,414 A | 1/1997 | Shipp et al. |
| 5,282,825 A | 2/1994 | Muck et al. | 5,593,424 A | 1/1997 | Northrup III |
| 5,290,289 A | 3/1994 | Sanders et al. | 5,597,378 A | 1/1997 | Jervis |
| 5,304,117 A | 4/1994 | Wilk | 5,601,571 A | 2/1997 | Moss |
| 5,304,204 A | 4/1994 | Bregen | 5,601,572 A | 2/1997 | Middleman et al. |
| 5,306,296 A | 4/1994 | Wright et al. | 5,601,600 A | 2/1997 | Ton |
| 5,312,436 A | 5/1994 | Coffey et al. | 5,603,718 A | 2/1997 | Xu |
| 5,314,468 A | 5/1994 | Ramos Martinez | 5,609,608 A | 3/1997 | Benett et al. |
| 5,330,503 A | 7/1994 | Yoon | 5,628,757 A | 5/1997 | Hasson |
| 5,334,196 A | 8/1994 | Scott et al. | 5,630,540 A | 5/1997 | Blewett |
| 5,336,233 A | 8/1994 | Chen | 5,632,752 A | 5/1997 | Buelna |
| 5,336,239 A | 8/1994 | Gimpelson | 5,632,753 A | 5/1997 | Loeser |
| 5,346,459 A | 9/1994 | Allen | 5,643,295 A | 7/1997 | Yoon |
| 5,350,420 A | 9/1994 | Cosgrove et al. | 5,643,305 A | 7/1997 | Al-Tameem |
| 5,353,804 A | 10/1994 | Kornberg et al. | 5,645,568 A | 7/1997 | Chervitz et al. |
| 5,355,897 A | 10/1994 | Pietrafitta et al. | 5,653,716 A | 8/1997 | Malo et al. |
| 5,356,424 A | 10/1994 | Buzerak et al. | 5,653,718 A | 8/1997 | Yoon |
| 5,364,406 A | 11/1994 | Sewell | 5,658,312 A | 8/1997 | Green et al. |
| 5,366,459 A | 11/1994 | Yoon | 5,660,186 A | 8/1997 | Bachir |
| 5,366,462 A | 11/1994 | Kaster et al. | 5,665,109 A | 9/1997 | Yoon |
| 5,366,479 A | 11/1994 | McGarry et al. | 5,669,918 A | 9/1997 | Balazs et al. |
| 5,374,268 A | 12/1994 | Sander | 5,676,670 A | 10/1997 | Kim |
| 5,376,096 A | 12/1994 | Foster | 5,683,417 A | 11/1997 | Cooper |
| 5,382,259 A | 1/1995 | Phelps et al. | 5,690,662 A | 11/1997 | Chiu et al. |
| 5,383,904 A | 1/1995 | Totakura et al. | 5,695,504 A | 12/1997 | Gifford, III et al. |
| 5,387,227 A | 2/1995 | Grice | 5,695,505 A | 12/1997 | Yoon |
| 5,403,331 A | 4/1995 | Chesterfield | 5,697,913 A | 12/1997 | Sierocuk et al. |
| 5,403,333 A | 4/1995 | Kaster et al. | 5,697,943 A | 12/1997 | Sauer et al. |
| 5,403,338 A | 4/1995 | Milo | 5,700,270 A | 12/1997 | Peyser et al. |
| 5,403,346 A | 4/1995 | Loeser | 5,700,271 A | 12/1997 | Whitfield et al. |
| 5,413,584 A | 5/1995 | Schulze | 5,702,412 A | 12/1997 | Popov et al. |
| 5,417,684 A | 5/1995 | Jackson et al. | 5,707,362 A | 1/1998 | Yoon |
| 5,417,700 A | 5/1995 | Egan | 5,707,380 A | 1/1998 | Hinchliffe et al. |
| 5,423,821 A | 6/1995 | Pasque | 5,709,693 A | 1/1998 | Taylor |
| 5,431,666 A | 7/1995 | Sauer et al. | 5,709,695 A | 1/1998 | Northrup, III |
| 5,437,680 A | 8/1995 | Yoon | 5,715,987 A | 2/1998 | Kelley et al. |
| 5,437,681 A | 8/1995 | Meade et al. | 5,720,755 A | 2/1998 | Dakov |
| 5,437,685 A | 8/1995 | Blasnik | 5,725,539 A | 3/1998 | Matern |
| 5,439,479 A | 8/1995 | Shichman et al. | 5,725,542 A | 3/1998 | Yoon |
| 5,445,167 A | 8/1995 | Yoon et al. | 5,728,135 A | 3/1998 | Bregen et al. |
| 5,445,644 A | 8/1995 | Pietrafitta et al. | 5,732,872 A | 3/1998 | Bolduc et al. |
| 5,450,860 A | 9/1995 | O'Connor | 5,735,290 A | 4/1998 | Sterman et al. |
| 5,451,231 A | 9/1995 | Rabenau et al. | 5,746,753 A | 5/1998 | Sullivan et al. |
| 5,452,733 A | 9/1995 | Sterman et al. | 5,755,778 A | 5/1998 | Kleshinski |
| 5,454,834 A | 10/1995 | Boebel et al. | 5,766,189 A | 6/1998 | Matsumo |
| 5,456,246 A | 10/1995 | Schmieding et al. | 5,769,870 A | 6/1998 | Salahich et al. |
| 5,462,561 A | 10/1995 | Voda | 5,779,718 A | 7/1998 | Green et al. |
| 5,474,557 A | 12/1995 | Mai | 5,782,397 A | 7/1998 | Koukline |
| 5,480,405 A | 1/1996 | Yoon | 5,782,844 A | 7/1998 | Yoon et al. |
| 5,486,187 A | 1/1996 | Schenck | 5,797,920 A | 8/1998 | Kim |
| 5,486,197 A | 1/1996 | Le et al. | 5,797,933 A | 8/1998 | Snow et al. |
| 5,488,958 A | 2/1996 | Topel et al. | 5,797,934 A | 8/1998 | Rygaard |
| 5,496,334 A | 3/1996 | Klundt et al. | 5,797,960 A | 8/1998 | Stevens et al. |
| 5,499,990 A | 3/1996 | Schulken et al. | 5,799,661 A | 9/1998 | Boyd et al. |
| 5,500,000 A | 3/1996 | Feagin et al. | 5,799,857 A | 9/1998 | Robertson et al. |
| 5,522,884 A | 6/1996 | Wright | 5,810,848 A | 9/1998 | Hayhurst |

| | | | | | | |
|---|---|---|---|---|---|---|
| 5,810,851 | A | 9/1998 | Yoon | 6,063,070 A | 5/2000 | Eder |
| 5,810,853 | A | 9/1998 | Yoon | 6,066,148 A | 5/2000 | Rygaard |
| 5,810,882 | A | 9/1998 | Bolduc et al. | 6,074,401 A | 6/2000 | Gardiner et al. |
| 5,817,113 | A | 10/1998 | Gifford, III et al. | 6,074,418 A | 6/2000 | Buchanan et al. |
| 5,820,631 | A | 10/1998 | Nobles | 6,077,291 A | 6/2000 | Das |
| 5,824,002 | A | 10/1998 | Gentelia et al. | 6,080,114 A | 6/2000 | Russin |
| 5,824,008 | A | 10/1998 | Bolduc et al. | 6,083,237 A | 7/2000 | Huitema et al. |
| 5,827,265 | A | 10/1998 | Glinsky et al. | 6,106,538 A | 8/2000 | Shiber |
| 5,827,316 | A | 10/1998 | Young et al. | 6,110,188 A | 8/2000 | Narciso |
| 5,830,221 | A | 11/1998 | Stein et al. | 6,113,611 A | 9/2000 | Allen et al. |
| 5,830,222 | A | 11/1998 | Makower | 6,113,612 A | 9/2000 | Swanson et al. |
| 5,833,698 | A | 11/1998 | Hinchliffe | 6,120,524 A | 9/2000 | Taheri |
| 5,849,019 | A | 12/1998 | Yoon | 6,132,438 A | 10/2000 | Fleischmann et al. |
| 5,851,216 | A | 12/1998 | Allen | 6,139,540 A | 10/2000 | Rost et al. |
| 5,855,614 | A | 1/1999 | Stevens et al. | 6,143,004 A | 11/2000 | Davis et al. |
| 5,868,702 | A | 2/1999 | Stevens et al. | 6,149,658 A | 11/2000 | Gardiner et al. |
| 5,868,763 | A | 2/1999 | Spence et al. | 6,152,935 A | 11/2000 | Kammerer et al. |
| 5,871,528 | A | 2/1999 | Camps et al. | 6,152,937 A | 11/2000 | Peterson et al. |
| 5,879,371 | A | 3/1999 | Gardiner et al. | 6,159,165 A | 12/2000 | Ferrera et al. |
| 5,881,943 | A | 3/1999 | Heck et al. | 6,159,225 A | 12/2000 | Makower |
| 5,882,340 | A | 3/1999 | Yoon | 6,165,183 A | 12/2000 | Kuehn et al. |
| 5,891,130 | A | 4/1999 | Palermo et al. | 6,165,185 A | 12/2000 | Shennib et al. |
| 5,891,160 | A | 4/1999 | Williamson, IV et al. | 6,171,320 B1 | 1/2001 | Monassevitch |
| 5,893,369 | A | 4/1999 | LeMole | 6,171,321 B1 | 1/2001 | Gifford, III et al. |
| 5,893,865 | A | 4/1999 | Swindle et al. | 6,176,413 B1 | 1/2001 | Heck et al. |
| 5,893,886 | A | 4/1999 | Zegdi et al. | 6,176,864 B1 | 1/2001 | Chapman |
| 5,895,394 | A | 4/1999 | Kienzle et al. | 6,179,840 B1 | 1/2001 | Bowman |
| 5,904,697 | A | 5/1999 | Gifford, III et al. | 6,179,848 B1 | 1/2001 | Solem |
| 5,908,428 | A | 6/1999 | Scirica et al. | 6,179,849 B1 | 1/2001 | Yencho et al. |
| 5,911,352 | A | 6/1999 | Racenet et al. | 6,183,512 B1 | 2/2001 | Howanec et al. |
| 5,919,207 | A | 7/1999 | Taheri | 6,190,373 B1 | 2/2001 | Palermo et al. |
| 5,931,842 | A | 8/1999 | Goldsteen et al. | 6,193,733 B1 | 2/2001 | Adams |
| 5,941,434 | A | 8/1999 | Green | 6,193,734 B1 | 2/2001 | Bolduc et al. |
| 5,941,442 | A | 8/1999 | Geiste et al. | 6,197,037 B1 | 3/2001 | Hair |
| 5,941,888 | A | 8/1999 | Wallace et al. | 6,217,611 B1 | 4/2001 | Klostermeyer |
| 5,941,908 | A | 8/1999 | Goldsteen et al. | 6,221,083 B1 | 4/2001 | Mayer |
| 5,944,730 | A | 8/1999 | Nobles et al. | 6,241,738 B1 | 6/2001 | Dereume |
| 5,951,576 | A | 9/1999 | Wakabayashi | 6,241,741 B1 | 6/2001 | Duhaylongsod et al. |
| 5,951,600 | A | 9/1999 | Lemelson | 6,248,117 B1 | 6/2001 | Blatter |
| 5,954,735 | A | 9/1999 | Rygaard | 6,250,308 B1 | 6/2001 | Cox |
| 5,957,363 | A | 9/1999 | Heck | 6,254,615 B1 | 7/2001 | Bolduc et al. |
| 5,957,938 | A | 9/1999 | Zhu et al. | 6,269,819 B1 | 8/2001 | Oz et al. |
| 5,957,940 | A | 9/1999 | Tanner et al. | 6,280,460 B1 | 8/2001 | Bolduc et al. |
| 5,961,481 | A | 10/1999 | Sterman et al. | 6,283,979 B1 | 9/2001 | Mers Kelly et al. |
| 5,961,539 | A | 10/1999 | Northrup, III et al. | 6,283,993 B1 | 9/2001 | Cosgrove et al. |
| 5,964,772 | A | 10/1999 | Bolduc et al. | 6,296,622 B1 | 10/2001 | Kurz et al. |
| 5,964,782 | A | 10/1999 | Lafontaine et al. | 6,296,656 B1 | 10/2001 | Bolduc et al. |
| 5,972,024 | A | 10/1999 | Northrup, III et al. | 6,306,141 B1 | 10/2001 | Jervis |
| 5,976,159 | A | 11/1999 | Bolduc et al. | 6,332,893 B1 | 12/2001 | Mortier et al. |
| 5,976,161 | A | 11/1999 | Kirsch et al. | 6,346,074 B1 | 2/2002 | Roth |
| 5,976,164 | A | 11/1999 | Bencini et al. | 6,346,112 B2 | 2/2002 | Adams |
| 5,976,178 | A | 11/1999 | Goldsteen et al. | 6,350,269 B1 | 2/2002 | Shipp et al. |
| 5,984,917 | A | 11/1999 | Fleischmann et al. | 6,352,543 B1 | 3/2002 | Cole |
| 5,984,959 | A | 11/1999 | Robertson et al. | 6,358,258 B1 | 3/2002 | Arcia et al. |
| 5,989,242 | A | 11/1999 | Saadat et al. | 6,361,559 B1 | 3/2002 | Houser et al. |
| 5,989,268 | A | 11/1999 | Pugsley, Jr. et al. | 6,368,348 B1 | 4/2002 | Gabbay |
| 5,989,276 | A | 11/1999 | Houser et al. | 6,371,964 B1 | 4/2002 | Vargas et al. |
| 5,989,278 | A | 11/1999 | Mueller | 6,387,105 B1 | 5/2002 | Gifford, III et al. |
| 5,993,468 | A | 11/1999 | Rygaard | 6,391,038 B2 | 5/2002 | Vargas et al. |
| 5,997,556 | A | 12/1999 | Tanner | 6,402,764 B1 | 6/2002 | Hendricksen et al. |
| 6,001,110 | A | 12/1999 | Adams | 6,406,492 B1 | 6/2002 | Lytle |
| 6,007,544 | A | 12/1999 | Kim | 6,406,493 B1 | 6/2002 | Tu et al. |
| 6,010,531 | A | 1/2000 | Donlon et al. | 6,409,739 B1 | 6/2002 | Nobles et al. |
| 6,013,084 | A | 1/2000 | Ken et al. | 6,409,758 B2 | 6/2002 | Stobie et al. |
| 6,022,367 | A | 2/2000 | Sherts | 6,416,527 B1 | 7/2002 | Berg et al. |
| 6,024,748 | A | 2/2000 | Manzo et al. | 6,418,597 B1 | 7/2002 | Deschenes et al. |
| 6,032,849 | A | 3/2000 | Mastri et al. | 6,419,658 B1 | 7/2002 | Restelli et al. |
| 6,033,419 | A | 3/2000 | Hamblin, Jr. et al. | 6,419,681 B1 | 7/2002 | Vargas et al. |
| 6,036,699 | A | 3/2000 | Andreas et al. | 6,419,695 B1 | 7/2002 | Gabbay |
| 6,036,703 | A | 3/2000 | Evans et al. | 6,425,900 B1 | 7/2002 | Knodel et al. |
| 6,036,710 | A | 3/2000 | McGarry et al. | 6,428,550 B1 | 8/2002 | Vargas et al. |
| 6,042,607 | A | 3/2000 | Williamson et al. | 6,428,555 B1 | 8/2002 | Koster, Jr. |
| 6,056,751 | A | 5/2000 | Fenton | 6,451,048 B1 | 9/2002 | Berg et al. |

| | | | | | | |
|---|---|---|---|---|---|---|
| 6,461,320 | B1 | 10/2002 | Yencho et al. | 2003/0093118 A1 | 5/2003 | Ho et al. |
| 6,475,222 | B1 | 11/2002 | Berg et al. | 2003/0125755 A1 | 7/2003 | Schaller et al. |
| 6,478,804 | B2 | 11/2002 | Vargas et al. | 2003/0191481 A1 | 10/2003 | Nguyen et al. |
| 6,485,496 | B1 | 11/2002 | Suyker et al. | 2003/0195531 A1 | 10/2003 | Nguyen et al. |
| 6,491,707 | B2 * | 12/2002 | Makower et al. ............ 606/153 | 2003/0199974 A1 | 10/2003 | Lee et al. |
| 6,497,671 | B2 | 12/2002 | Ferrera et al. | 2004/0050393 A1 | 3/2004 | Golden et al. |
| 6,497,710 | B2 | 12/2002 | Yencho et al. | 2004/0068276 A1 | 4/2004 | Golden et al. |
| 6,514,265 | B2 | 2/2003 | Ho et al. | 2004/0102797 A1 | 5/2004 | Golden et al. |
| 6,517,558 | B2 | 2/2003 | Gittings et al. | 2004/0111099 A1 | 6/2004 | Nguyen et al. |
| 6,524,338 | B1 | 2/2003 | Gundry | 2004/0138685 A1 | 7/2004 | Clague et al. |
| 6,533,812 | B2 | 3/2003 | Swanson et al. | 2004/0176663 A1 | 9/2004 | Edoga |
| 6,537,288 | B2 | 3/2003 | Vargas et al. | 2004/0193259 A1 | 9/2004 | Gabbay |
| 6,547,799 | B2 | 4/2003 | Hess et al. | 2005/0004582 A1 | 1/2005 | Edoga |
| 6,551,332 | B1 | 4/2003 | Nguyen et al. | 2005/0021054 A1 | 1/2005 | Ainsworth et al. |
| 6,562,053 | B2 | 5/2003 | Schulze et al. | 2005/0043749 A1 | 2/2005 | Breton et al. |
| 6,575,985 | B2 | 6/2003 | Knight et al. | 2005/0065601 A1 | 3/2005 | Lee et al. |
| 6,589,255 | B2 | 7/2003 | Schulze et al. | 2005/0070924 A1 | 3/2005 | Schaller et al. |
| 6,607,541 | B1 | 8/2003 | Gardiner et al. | 2005/0075659 A1 | 4/2005 | Realyvasquez et al. |
| 6,607,542 | B1 | 8/2003 | Wild et al. | 2005/0075667 A1 | 4/2005 | Schaller et al. |
| 6,613,059 | B2 | 9/2003 | Schaller et al. | 2005/0080454 A1 | 4/2005 | Drews |
| 6,629,988 | B2 | 10/2003 | Weadock | 2005/0101975 A1 | 5/2005 | Nguyen et al. |
| 6,635,214 | B2 | 10/2003 | Rapacki et al. | 2005/0107871 A1 | 5/2005 | Realyvasquez et al. |
| 6,641,593 | B1 | 11/2003 | Schaller et al. | 2005/0131429 A1 | 6/2005 | Ho et al. |
| 6,648,900 | B2 | 11/2003 | Fleischman et al. | 2005/0267572 A1 | 12/2005 | Schoon et al. |
| 6,651,670 | B2 | 11/2003 | Rapacki et al. | 2006/0004389 A1 | 1/2006 | Nguyen et al. |
| 6,651,672 | B2 | 11/2003 | Roth | 2006/0253143 A1 | 11/2006 | Edoga |
| 6,652,540 | B1 | 11/2003 | Cole et al. | 2006/0271081 A1 | 11/2006 | Realyvasquez |
| 6,652,541 | B1 | 11/2003 | Vargas et al. | 2006/0293701 A1 | 12/2006 | Ainsworth et al. |
| 6,660,015 | B1 | 12/2003 | Berg et al. | 2007/0010835 A1 | 1/2007 | Breton et al. |
| 6,682,540 | B1 | 1/2004 | Sancoff et al. | 2007/0027461 A1 | 2/2007 | Gardiner et al. |
| 6,695,859 | B1 | 2/2004 | Golden et al. | 2007/0106313 A1 | 5/2007 | Golden et al. |
| 6,702,826 | B2 | 3/2004 | Liddicoat et al. | 2007/0142848 A1 | 6/2007 | Ainsworth et al. |
| 6,709,442 | B2 | 3/2004 | Miller et al. | | | |
| 6,712,829 | B2 | 3/2004 | Schulze | | FOREIGN PATENT DOCUMENTS | |
| 6,719,768 | B1 | 4/2004 | Cole et al. | DE | 0377052 | 6/1923 |
| 6,743,243 | B1 | 6/2004 | Roy et al. | DE | 27 03 529 | 1/1977 |
| 6,749,622 | B2 | 6/2004 | McGuckin et al. | DE | 32 03 410 | 5/1981 |
| 6,776,782 | B2 | 8/2004 | Schulze | DE | 32 27 984 | 2/1984 |
| 6,776,784 | B2 | 8/2004 | Ginn | DE | 3504202 | 8/1985 |
| 6,776,785 | B1 | 8/2004 | Yencho et al. | DE | 41 33 800 | 10/1991 |
| 6,802,847 | B1 | 10/2004 | Carson et al. | DE | 44 02 058 | 4/1995 |
| 6,821,286 | B1 | 11/2004 | Carranza et al. | DE | 19 547 617 | 9/1997 |
| 6,869,444 | B2 | 3/2005 | Gabbay | DE | 19732234 | 1/1999 |
| 6,913,607 | B2 | 7/2005 | Ainsworth et al. | EP | 0072232 | 2/1983 |
| 6,918,917 | B1 | 7/2005 | Nguyen et al. | EP | 0122046 | 3/1983 |
| 6,921,407 | B2 | 7/2005 | Nguyen et al. | EP | 0129441 | 12/1984 |
| 6,926,730 | B1 | 8/2005 | Nguyen et al. | EP | 0130037 | 1/1985 |
| 6,945,980 | B2 | 9/2005 | Nguyen et al. | EP | 0 140 557 A2 | 5/1985 |
| 6,955,679 | B1 | 10/2005 | Hendricksen et al. | EP | 0 121 362 B1 | 9/1987 |
| 6,960,221 | B2 | 11/2005 | Ho et al. | EP | 0409569 | 1/1991 |
| 6,979,337 | B2 | 12/2005 | Kato | EP | 0 432 692 A1 | 6/1991 |
| 6,979,338 | B1 | 12/2005 | Loshakove et al. | EP | 0 478 949 B1 | 8/1991 |
| 7,022,131 | B1 | 4/2006 | Derowe et al. | EP | 0 494 636 A1 | 7/1992 |
| 7,056,330 | B2 | 6/2006 | Gayton | EP | 0 559 429 A1 | 3/1993 |
| 7,063,711 | B1 | 6/2006 | Loshakove et al. | EP | 0598529 | 5/1994 |
| 7,070,618 | B2 | 7/2006 | Streeter | EP | 0 326 426 B1 | 12/1994 |
| 7,182,769 | B2 | 2/2007 | Ainsworth et al. | EP | 0 419 597 B1 | 12/1994 |
| 7,220,268 | B2 | 5/2007 | Blatter | EP | 0632999 | 1/1995 |
| 2001/0018592 | A1 | 8/2001 | Schaller et al. | EP | 0 641 546 A1 | 3/1995 |
| 2001/0018593 | A1 | 8/2001 | Nguyen et al. | EP | 0656191 | 6/1995 |
| 2001/0018611 | A1 | 8/2001 | Solem et al. | EP | 0687446 | 12/1995 |
| 2001/0021856 | A1 | 9/2001 | Bolduc et al. | EP | 0705568 | 4/1996 |
| 2001/0047181 | A1 | 11/2001 | Ho et al. | EP | 0 711 532 A1 | 5/1996 |
| 2002/0010490 | A1 | 1/2002 | Schaller et al. | EP | 0 734 697 A2 | 10/1996 |
| 2002/0042623 | A1 | 4/2002 | Blatter et al. | EP | 0705569 | 10/1996 |
| 2002/0082614 | A1 | 6/2002 | Logan et al. | EP | 0 537 955 B1 | 12/1996 |
| 2002/0099395 | A1 | 7/2002 | Acampora et al. | EP | 0 778 005 A1 | 6/1997 |
| 2002/0151916 | A1 | 10/2002 | Muramatsu et al. | EP | 0 815 795 A1 | 1/1998 |
| 2002/0165561 | A1 | 11/2002 | Ainsworth et al. | GB | 2 223 410 | 4/1990 |
| 2002/0173803 | A1 | 11/2002 | Yang et al. | JP | 07308322 | 11/1995 |
| 2003/0074012 | A1 | 4/2003 | Nguyen et al. | JP | 08336544 | 12/1996 |
| 2003/0078603 | A1 | 4/2003 | Schaller et al. | JP | 10337291 | 12/1998 |
| 2003/0083742 | A1 | 5/2003 | Spence et al. | | | |

| | | |
|---|---|---|
| RU | 2110222 C1 | 5/1998 |
| SU | 577022 | 10/1977 |
| SU | 1186199 A | 10/1985 |
| SU | 1456109 A1 | 2/1989 |
| SU | 1560133 A1 | 4/1990 |
| WO | WO 90/06725 | 6/1990 |
| WO | WO 90/09149 | 8/1990 |
| WO | WO 90/14795 | 12/1990 |
| WO | 91/08708 | 6/1991 |
| WO | WO 91/07916 | 6/1991 |
| WO | WO 91/17712 | 11/1991 |
| WO | WO 92/05828 | 4/1992 |
| WO | 92/12676 | 8/1992 |
| WO | 92/22041 | 12/1992 |
| WO | 93/01750 | 2/1993 |
| WO | WO 94/15535 | 7/1994 |
| WO | WO 94/15537 | 7/1994 |
| WO | WO 96/00035 | 1/1996 |
| WO | WO 96/06565 | 3/1996 |
| WO | WO 96/38090 | 12/1996 |
| WO | 97/12555 | 4/1997 |
| WO | 97/16122 | 5/1997 |
| WO | 97/27898 | 8/1997 |
| WO | WO 97/28744 | 8/1997 |
| WO | 97/31575 | 9/1997 |
| WO | WO 97/32526 | 9/1997 |
| WO | 97/40754 | 11/1997 |
| WO | WO 97/42881 | 11/1997 |
| WO | 98/19636 | 5/1998 |
| WO | WO 98/30153 A1 | 7/1998 |
| WO | WO 98/42262 A1 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/59380 | 10/2000 |
| WO | 00/60995 | 10/2000 |
| WO | 00/64381 | 11/2000 |
| WO | 00/74603 | 12/2000 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Wylie, e. J. et al., (1980). *Manual of Vascular Surgery*. R.H. Egdahl ed., New York: Springer-Verlag, vol. 1 and 2, 10 pages. Title pages and table of contents only.

Robert W. Emery, MD et al. Techniques for Mimimally Invasive Direct Coronary Artery Bypass (MIDCAB) Surgery, "Suture Techniques for MIDCAB Surgery" Chapt 12, 87-91 (Robert W. Emery, MD ed. 1997).

Written Opinion PCT /US99/12566 (Jul. 28, 2000).

Chitwood Jr., Mitral Valve Repair: Ischemic, Mastery of Cardiothoracic Surgery, Lippencott-Raven Publishers, 1998, Chapter 32, pp. 309-321.

Grondin, et al., Carpentier's Annulus and De Vega's Annuloplasty: The end of the tricuspid challenge, No. 1975, vol. 70, pp. 852-861.

Holper, et al., Surgery For Tricuspid Insufficiency: Long Term Follow-Up After De Vega Annuloplasty, Thorac Cardiovasc Surgeon, 41, 1993.

Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.

Rabago, et al., The New De Vega Technique In Tricuspid Annuloplasty: Results in 150 patients, J. Cardiovas Surg. 1980, 21 pp. 231-238.

Rivera, et al., Carpentier's Flexible Ring Versus De Vega's Annuloplasty, J Thorac Cardiovas Surg, Feb. 1985, 89 pp. 196-203.

Wei, et al., De Vega's Semicircular Annuloplasty For Tricuspid Valve Regurgitation, Ann Thorac Surg, 1993, 55: pp. 482-485.

Wylie, et al., Manual of Vascular Surgery, R. H. Egdahl ed. Spring-Verlag: New York, vol. II, 1986, Table of Contents only.

Wylie, et al., Manual of Vascular Surgery, Springer-Verlag New York, vol. I, 1980, Table of Contents only.

Yun, et al. Mitral Valve Replacement, Mastery of Cardiothoracic Surgery, Lippencott-Raven Publishers, 1998, Chapter 34, pp. 329-341.

International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report On Patentability PCT/US2004/023728.
US 6,503,260, 01/2003, Schaller et al. (withdrawn)

* cited by examiner

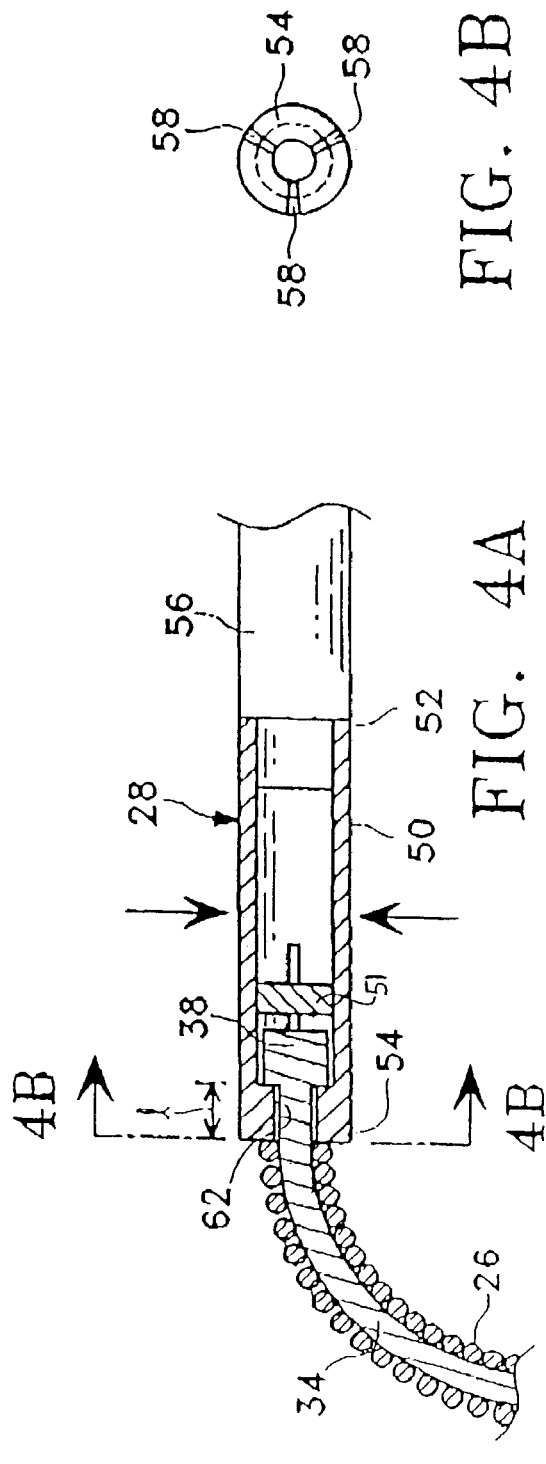
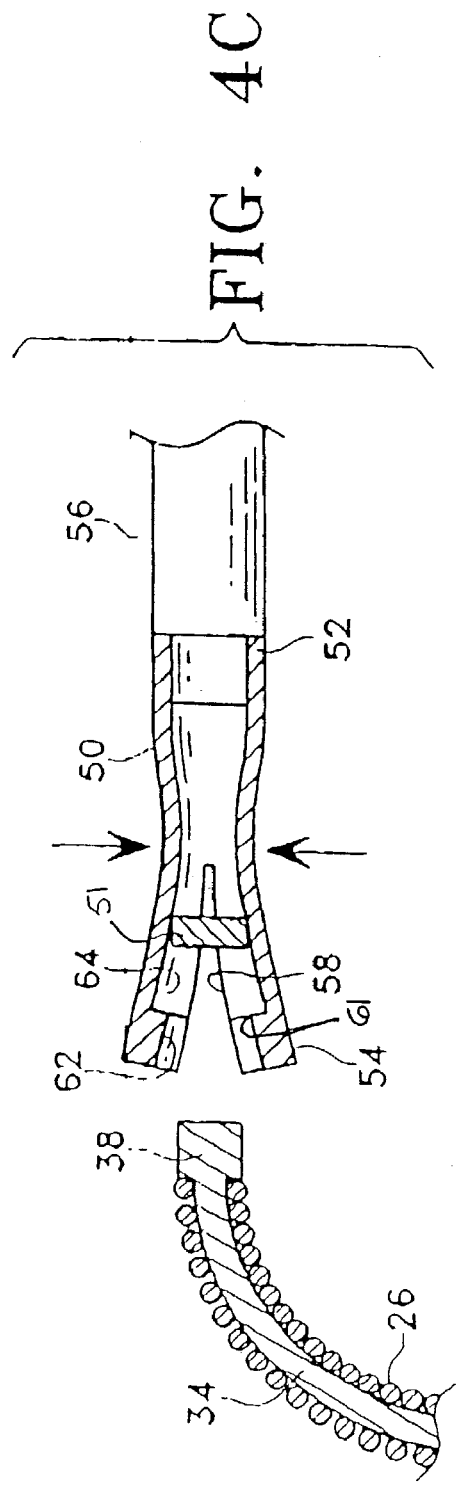
FIG. 4A
FIG. 4B
FIG. 4C

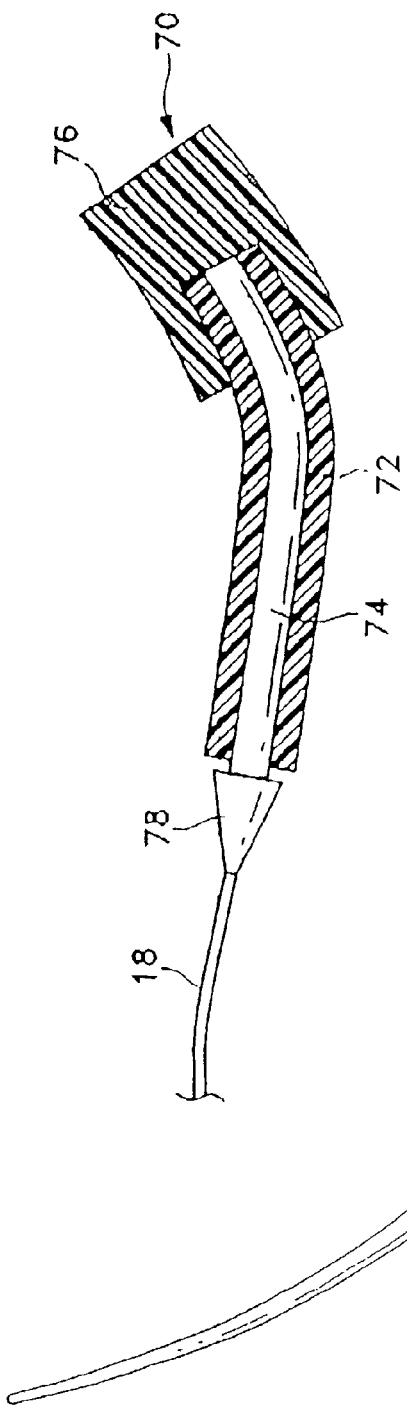
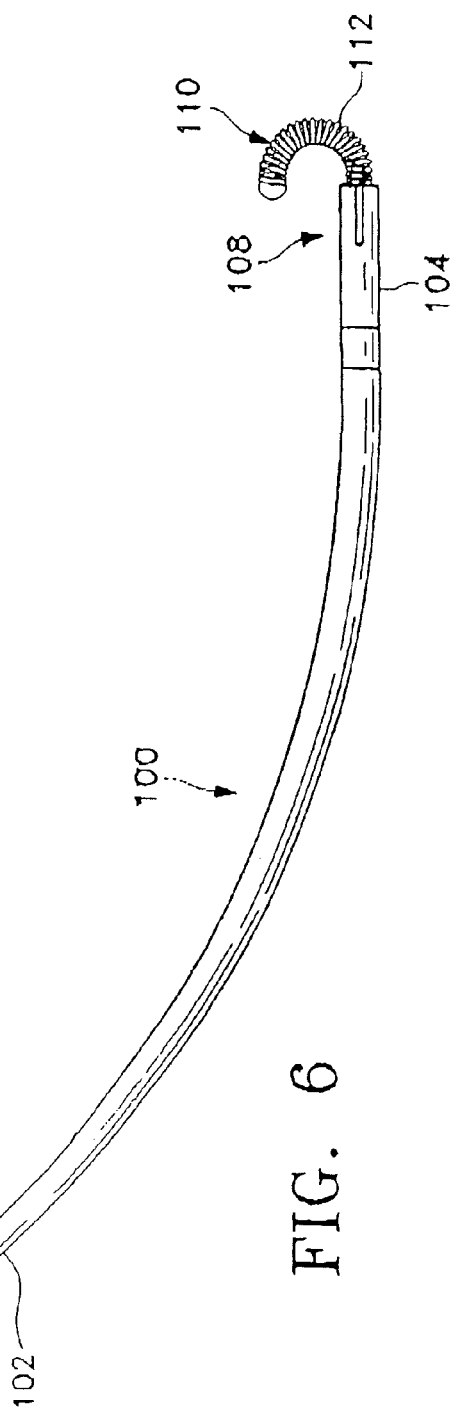
FIG. 5
FIG. 6

TISSUE CONNECTOR APPARATUS AND METHODS

CROSS REFERENCE TO RELATED APPLICATION(S)

This application is a continuation of U.S. patent application Ser. No. 09/089,884, entitled Tissue Connector Apparatus and Methods and filed Jun. 3, 1998, now U.S. Pat. No. 6,607,541, which application is incorporated by reference in its entirety and to which we claim priority under 35 U.S.C. §120.

FIELD OF THE INVENTION

The present invention relates to instruments and methods for connecting body tissues, or body tissue to prostheses.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5-10 millimeters, and sometimes up to as much as 20 millimeters. A number of such cannulas are inserted for any given operation.

A viewing instrument, typically including a miniature video camera or optical telescope, is inserted through one of these cannulas and a variety of surgical instruments and refractors are inserted through others. The image provided by the viewing device may be displayed on a video screen or television monitor, affording the surgeon enhanced visual control over the instruments Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine, or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both the graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

A parachuting technique may be used to align the graft with the artery in an end-to-side anastomosis procedure. One or multiple sutures are attached to the graft and artery and are used to pull or "parachute" the graft vessel into alignment with an opening formed in a sidewall of the artery. A drawback to this procedure is the difficulty in preventing the suture from tangling and the time and surgical skill required to tie individual knots when using multiple sutures. Due to space requirements, this procedure is generally limited to open surgery techniques.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for widespread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connecting systems.

SUMMARY OF THE INVENTION

The present invention involves apparatus and methods for connecting material, at least one of which is tissue. The invention may, for example, be used to secure one vessel to another, such as in a vascular anastomosis.

According to one aspect of the invention, a tissue connector assembly is provided and comprises a flexible member and a surgical clip which may be releasably coupled to the flexible member. With this construction, a needle may be coupled to the flexible member, which may be in the form of a suture, to facilitate, for example, parachuting suture tissue connecting procedures. The surgical clip may eliminate the need for tying sutures, which requires significant skill, space, and time.

According to another aspect of the invention a tissue connector assembly comprises a needle, a flexible member coupled to the needle, and a locking device coupled to the flexible member. The locking device is adapted for receiving a surgical fastener. Thus, a surgical fastener may be selected based on a desired procedure and coupled to the locking device to facilitate, for example, parachuting suture tissue connecting procedures as discussed above.

According to another aspect of the invention, a method for connecting tissues includes drawing portions of tissue together with a clip assembly and securing the tissue portions together with the clip assembly.

According to another aspect of the invention, multiple portions of material are drawn together with a tissue connector assembly having a clip in an open position. At least one of the portions of material is tissue. The clip is closed to secure the material portions therein. The materials may be drawn together by pulling the tissue connector assembly with at least a portion of the clip positioned in the materials. A needle may be used to insert the tissue connector assembly into the material. A portion of the tissue connector assembly may be manipulated to simultaneously actuate closure of the clip and release the needle from the clip.

According to another aspect of the invention, a tissue connector assembly is inserted through graft and target vessels with the graft vessel being spaced from the target vessel. The tissue connector assembly has a first end extending from an exterior surface of the graft vessel and a second end extending from an exterior surface of the target vessel. At least one end of the tissue connector assembly is pulled to draw the graft vessel into contact with the target vessel.

According to another aspect of the invention, a tissue connector assembly is inserted through the graft and target vessels with the graft vessel being spaced from the target vessel and the tissue connector assembly having a first end extending from an exterior surface of the graft vessel and a second end extending from an exterior surface of the target vessel. At least a portion of the tissue connector assembly is pulled to draw the graft vessel into contact with the target vessel.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 4A is a cross-sectional view of a restraining device of the tissue connector assembly of FIG. 1 in a locked position;

FIG. 4B is a cross-sectional view of the restraining device of FIG. 4A taken in the plane including line 4B-4B;

FIG. 4C is a cross-sectional view of the restraining device of FIG. 4A in an unlocked position;

FIG. 5 is an alternate embodiment of the restraining device of FIG. 4A; and

FIG. 6 is a front view of a second embodiment of a tissue connector assembly of the present invention shown in an open position.

Corresponding reference characters indicate corresponding parts throughout the several views of the drawings.

DESCRIPTION OF THE INVENTION

Figure 1:
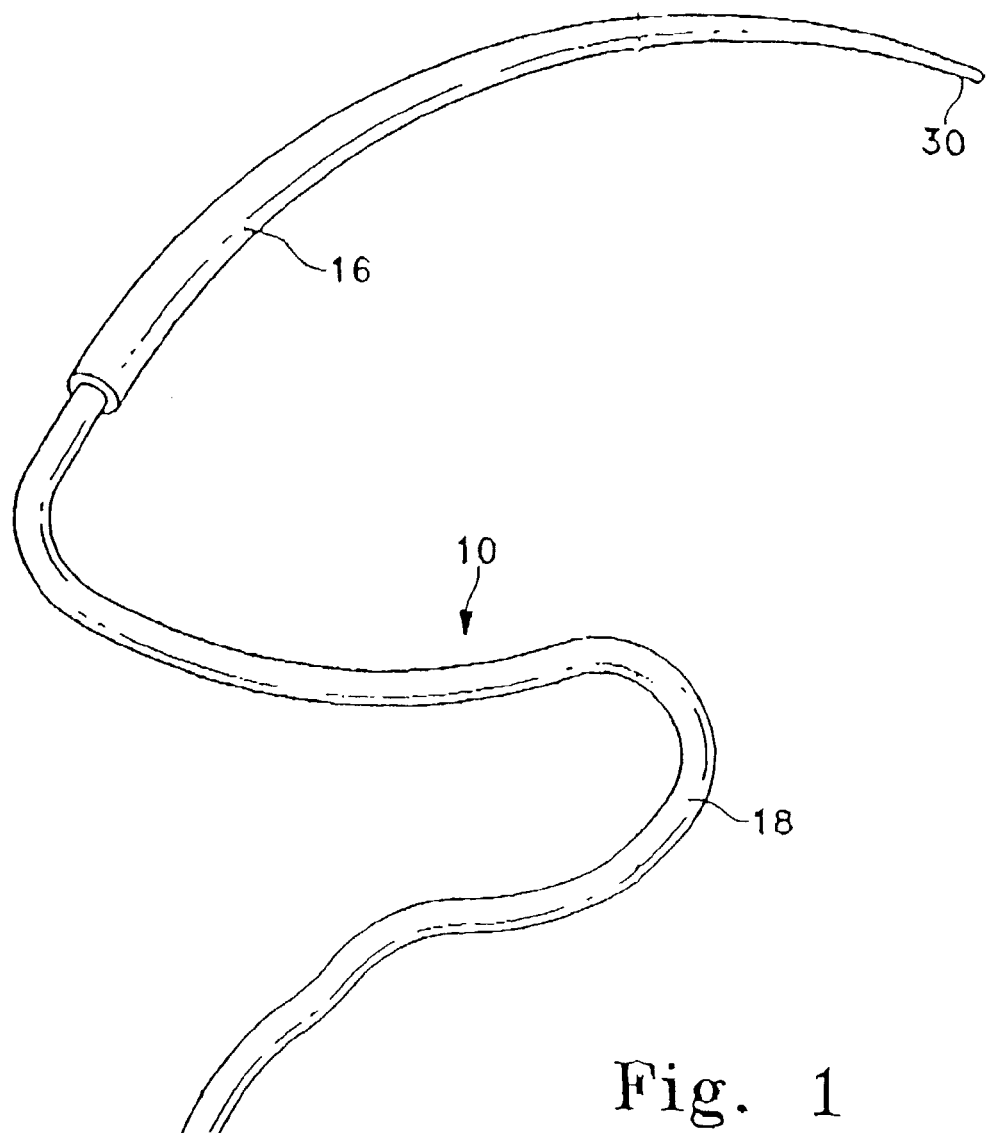
FIG. 1 is a perspective of a tissue connector assembly of the present invention.

Referring now to the drawings, and first to FIG. 1, a tissue connector assembly constructed according to the principles of the present invention is shown and generally indicated with reference numeral 10. The tissue connector assembly 10 may be used to manipulate and align tissues, or tissue and prosthesis with respect to each other and thereafter connect the tissues or tissue and prosthesis together (FIGS. 2A-2G). As used herein, the term graft includes any of the following: homografts, xenografts, allografts, alloplastic materials, and combinations of the foregoing. The tissue connector assembly 10 may be used in vascular surgery to replace or bypass a diseased, occluded, or injured artery by connecting a graft vessel 12 to a coronary artery 14 or vein in an anastomosis, for example. The tissue connector assembly 10 may be used in open surgical procedures or in minimally invasive or endoscopic procedures for attaching tissue located in the chest, abdominal cavity, or retroperitoneal space. These examples, however, are provided for illustration and are not meant to be limiting.

In the embodiment shown in FIG. 1, the tissue connector assembly 10 generally comprises a penetrating member 16, flexible member 18, and fastener or surgical clip 20 (FIG. 1). A restraining device, generally indicated at 24 and comprising a spring (or coil) 26 and a locking device (coupling member) generally indicated at 28, is connected to the fastener 20 for holding the fastener in a deformed configuration as further described below. Although a particular fastener and accompanying restraining device is shown in FIG. 1, it should be understood that any suitable fastener can be used, including but not limited to the alternate fastener configurations described below. For example, the fastener or surgical clip may be a plastically deformable clip or may comprise two or more parts, at least one of which is movable relative to the other part, such as with a hinged clip.

The penetrating member or needle 16 has a sharp pointed tip 30 at its distal end for penetrating tissue. The needle 16 may be bent as shown in FIG. 1, for example. The diameter of at least a portion of the needle 16 is preferably greater than the diameter of the flexible member 18 so that the flexible member can easily be pulled through an opening formed in the tissue by the needle. The distal end of the needle 16 is preferably rigid to facilitate penetration of tissue. The remaining length of the needle 16 may be rigid or flexible to facilitate movement of the needle through the tissue as further described below. The tip 30 of the needle 16 may be conical, tapered, or grounded to attain a three or four facet tip, for example. The needle 16 may be made from stainless steel or any other suitable material, such as a polymeric material. It is to be understood that the needle 16 may have a shape or radius of curvature other than the one shown, without departing from the scope of the invention. The needle 16 may also be integrally formed with the flexible member 18 (e.g., both needle and flexible member formed of the same material.)

The flexible member 18 may be in the form of a suture formed from conventional filament material, metal alloy such as nitinol, polymeric material, or any other suitable material. The material may be non-stretchable or stretchable, solid or hollow, and have various cross-sectional diameters. The suture may have a cross-sectional diameter of 0.003 inch, for example. The diameter and length of the suture will vary depending on the specific application. The suture may be attached to the needle 16 by crimping or swaging the needle onto the suture, gluing the suture to the needle, or any other suitable attachment method. The flexible member 18 may have cross-sectional shapes other than the one shown herein.

One embodiment of a fastener comprises a deformable wire 34 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire 34 is in its deformed configuration. As the stress is removed, the material undergoes a martensitic to austenitic conversion and springs back to its original undeformed configuration. When the wire 34 is positioned within the tissue in its undeformed configuration, a residual stress is present to maintain the tissue tightly together (FIG. 2E). In order for the pseudoelastic wire 34 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius).

It is to be understood that the shape memory alloy may also be heat activated, or a combination of heat activation and pseudoelastic properties may be used, as is well known by those skilled in the art.

Figure 3A:
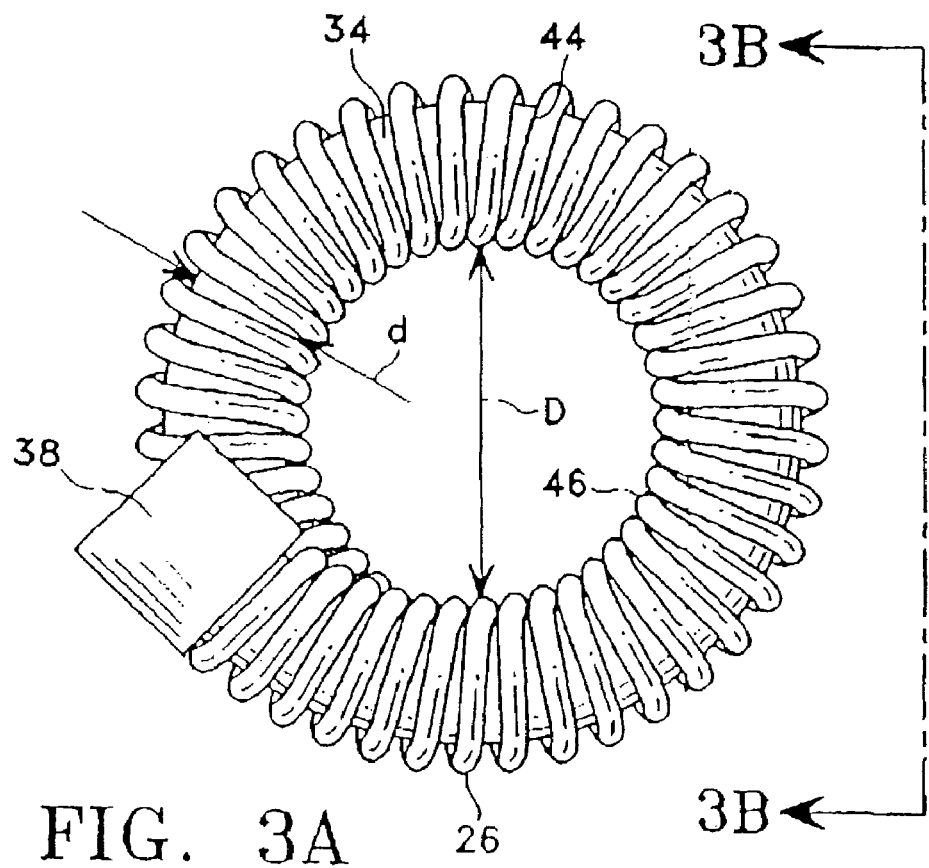
FIG. 3A is an enlarged view of a fastener of the tissue connector assembly of FIG. 1 shown in a closed position.

The cross-sectional diameter of the wire 34 and length of the wire will vary depending on the specific application. The diameter d of the wire 34 may be, for example, between 0.001 and 0.015 inch. For coronary bypass applications, the diameter is preferably between 0.001 and 0.008 inch with a diameter D of the loop being between 0.0125 and 0.0875 inch (FIG. 3A). As shown in FIG. 3A, the wire 34 has a circular cross-sectional shape. The diameter D of the loop of the fastener 20 in its closed position is preferably sized to prevent movement between adjacent tissues. It is to be understood, however, that the wire may have other cross-sectional shapes such as rectangular, or may be formed from multiple strands without departing from the scope of the invention.

The proximal end of the wire 34 may include a stop 36 having a cross-sectional area greater than the cross-sectional area of the wire and coil 26 to prevent the wire and coil from passing through the tissue. The stop 36 may be attached to the end of the wire 34 by welding, gluing or other suitable attachment means or may be formed integrally with the wire by deforming the end of the wire. The stop 36 may also be eliminated to facilitate pulling the fastener completely through the tissue, if, for example, the entire fastener needs to be removed from the vessel during the insertion procedure. The distal end of the wire 34 includes an enlarged portion 38 for engagement with the restraining device 24 as further described below (FIG. 4A). The enlarged portion 38 may be formed by deforming the end of the wire 34 by swaging or arc welding, or attaching by welding, swaging, or other suitable means an enlarged portion to the end of the wire.

Figure 3B:
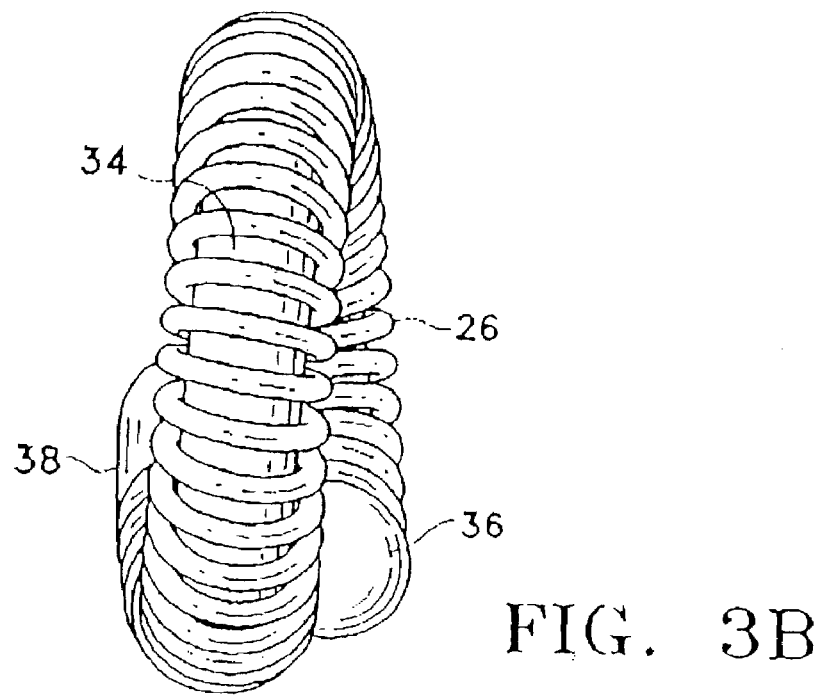
FIG. 3B is a side view of the fastener of FIG. 3A.

The wire 34 has an undeformed or closed configuration (position, state) (FIG. 3A) for keeping or connecting tissue together, and a deformed or open configuration (position, state) (FIG. 3C) for insertion of the wire into tissue. As discussed above, the wire 34 is in its closed configuration when in a relaxed state. The wire 34 is preferably not deformed past its yield point in its open position. Accordingly, it may have a U-shaped configuration in its open position to facilitate insertion of the wire through the tissue. It is to be understood that U-shaped configuration may be alternatively substituted by an equivalent structure such as C-shaped, V-shaped, J-shaped, and other similarly shaped configurations. The wire 34 is moved from its closed position to its open position by a restraining device, as further described below. When in its closed position, the wire 34 forms a loop with the ends of the wire in a generally side-by-side or overlapping orientation (FIG. 3B).

The wire 34 may be formed in the above described shape by first wrapping the wire onto a mandrel and heat treating the wire at approximately 400-500 degrees Celsius for approximately 5 to 30 minutes. The wire 34 is then air quenched at room temperature. The mandrel may have a constant diameter or may be conical in shape.

Figure 3C:
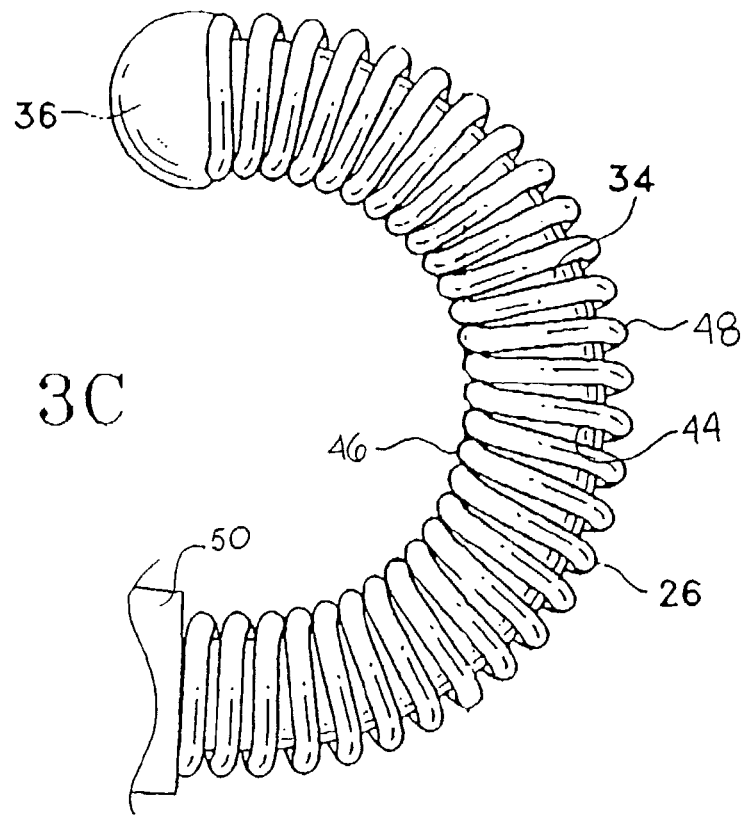
FIG. 3C is an enlarged view of the fastener in an open position.
Figure 3D:
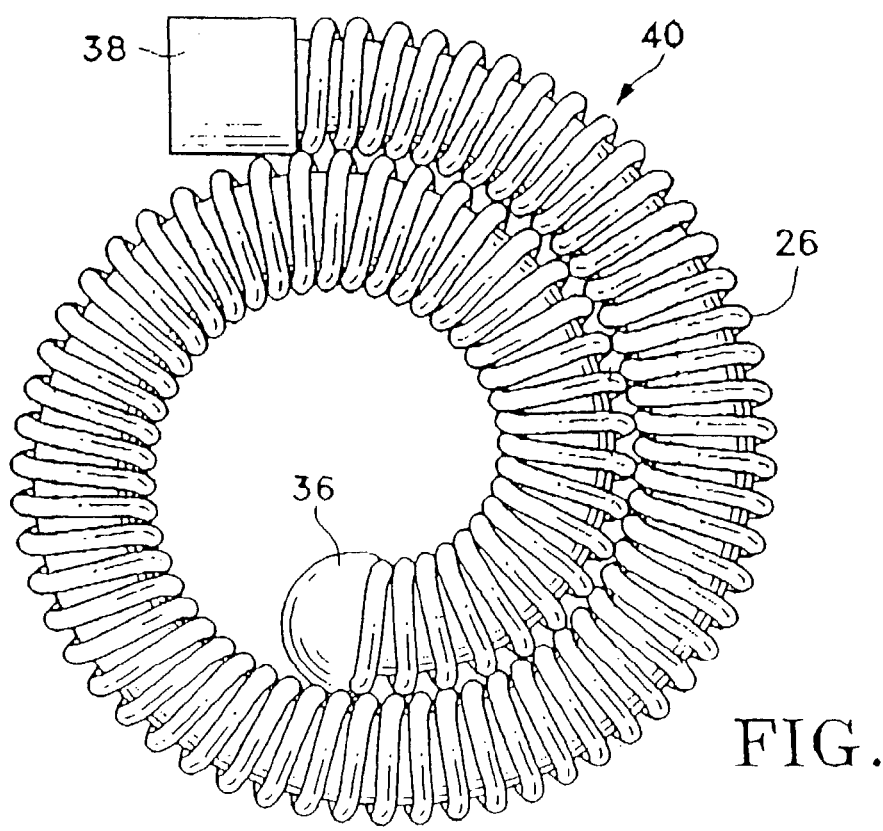
FIG. 3D is an enlarged view of an alternate configuration of the fastener shown in a closed position.

An alternate configuration of the surgical clip 20 in its closed position is shown in FIG. 3D, and generally indicated at 40. The fastener 40 forms a spiral configuration in its closed position for trapping the tissue within a loop formed by the spiral. In its open position, the fastener 40 is configured to form less than a full 360 degree turn.

Figure 3E:
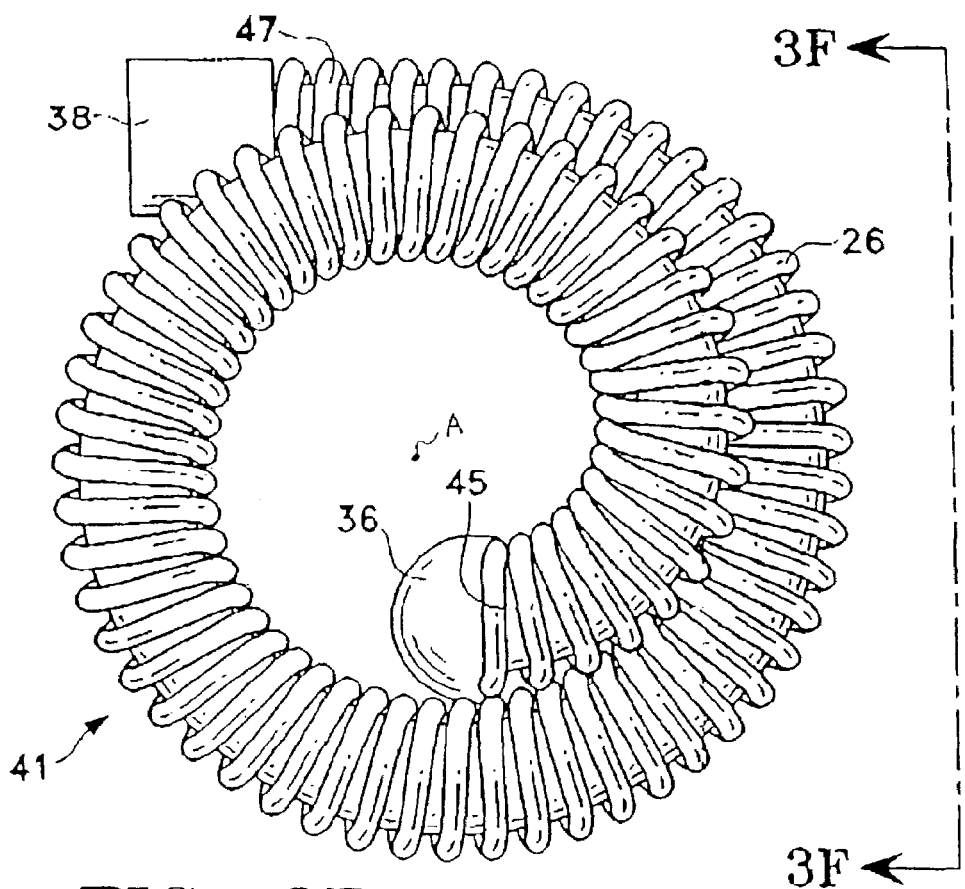
FIG. 3E is an enlarged view of an alternate configuration of the fastener shown in a closed position.
Figure 3F:
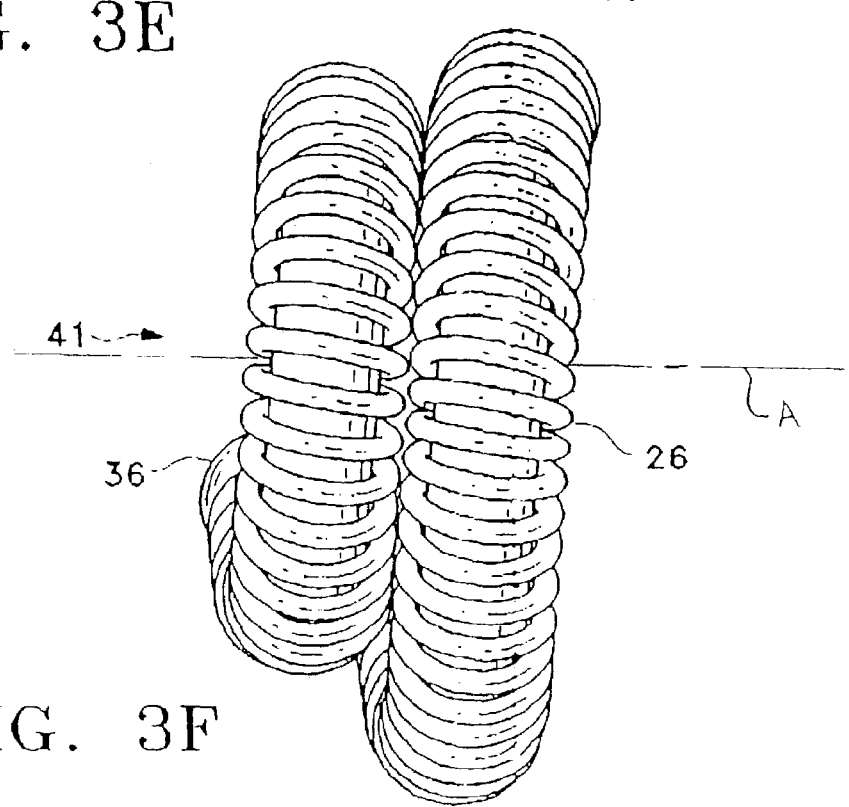
FIG. 3F is a side view of the fastener of FIG. 3E.

Another alternate configuration of the surgical clip 20 is shown in FIGS. 3E and 3F in its closed position, and is generally indicated at 41. The fastener 41 is formed in a spiral about a central longitudinal axis A. As shown in FIG. 3F, the fastener 41 has a generally conical shape along the longitudinal axis A, with a decreasing diameter as the radius of curvature of the fastener 41 decreases. The fastener 41 has an inner end portion 45 and an outer end portion 47, with the enlarged portion 38 of the wire being disposed at the outer end portion for engagement with the restraining device 24.

Figure 3G:
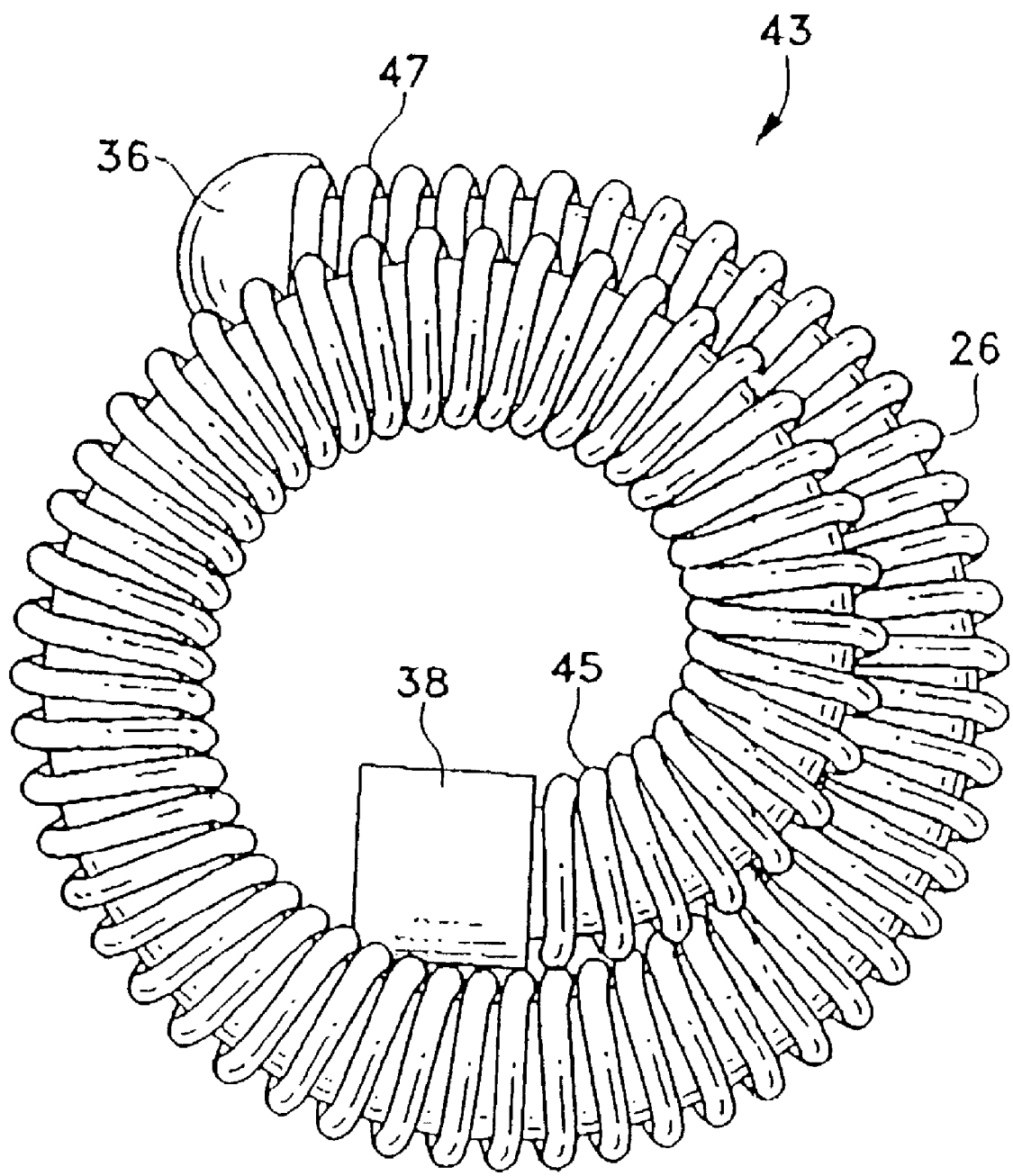
FIG. 3G is an enlarged view of an alternate configuration of the fastener shown in a closed position.

A modification of the fastener 41 is shown in FIG. 3G, and generally indicated at 43. The fastener 43 is similar to the fastener 41 described above, except that the enlarged portion 38, which is adapted for engaging a restraining device or releasable locking mechanism, is positioned at the inner end portion 45 of the fastener. Placement of the restraining device 24 at the inner end portion 45 of the fastener 43 increases the compression force of the wire in its undeformed position on the tissue and decreases the surface area of the fastener exposed to blood flow.

It is to be understood that the fastener 20, 40, 41, 43 may have undeformed or deformed configurations different than those shown herein without departing from the scope of the invention. In addition, a locking clip (not shown) may also be attached to connect the ends of the fastener 20, 40, 41, 43 when the fastener is in its closed position to prevent possible opening of the fastener over time. The locking clip may also be integrally formed with one end of the fastener.

As shown in FIG. 3C, the wire 34 is surrounded by the spring or coil 26 which, along with the locking device 28, restrains the wire in its deformed configuration. The coil 26 comprises a helical wire forming a plurality of loops which define a longitudinal opening 44 for receiving the shape memory alloy wire 34. The coil 26 may be formed from a platinum alloy wire having a cross-sectional diameter of approximately 0.0005-0.005 inch, for example. The helical wire may have other cross-sectional shapes and be formed of different materials. The coil 26 is preferably sized so that when in its free (uncompressed state) it extends the length of the wire 34 with one end adjacent the stop 36 at the proximal end of the wire and the other end adjacent the enlarged portion 38 at the distal end of the wire. It is to be understood that the coil may not extend the full length of the wire. For example, a flange or similar device may be provided on an intermediate portion of the wire 34 to limit movement of the coil along the length of the wire.

When the coil 26 is in its free state (with the wire in its undeformed configuration), loops of the coil are generally spaced from one another and do not exert any significant force on the wire 34 (FIG. 3A). When the coil 26 is compressed (with the wire 34 in its deformed configuration), loops of the coil on the inner portion 46 of the coil are squeezed together with a tight pitch so that the loops are contiguous with one another while loops on the outer portion 48 of the coil are spaced from one another (FIG. 3C). This is due to the compressed inner arc length of the coil 26 and the expanded outer arc length of the coil. The compression of the loops on the inner portion 46 of the coil 26 exerts a force on the inner side of the wire 34 which forces the wire to spread open (i.e., tends to straighten the wire from its closed configuration to its open configuration). The end of the coil 26 adjacent the stop 36 is held in a fixed position relative to the wire 34. The opposite end of the coil 26 is free to move along the wire 34 and is held in place when the coil is in its compressed position by the locking device 28.

The locking device 28 of the embodiment shown in FIGS. 1 and 4A-4C comprises a flexible tubular member 50 having a distal end portion 52 coupled to the flexible member 18 and a proximal end portion 54 releasably attached to the wire. The locking device 28 couples the flexible member 18 and needle 16 to the clip 20. In addition to releasably coupling the flexible member 18 and needle 16 to the clip 20, the locking device compresses the coil 26 to bias the clip 20 in its open configuration. The distal end 52 of the tubular member 50 is attached to the flexible member 18 with a tapered portion or transition sleeve 56 extending from the tubular member to the suture to facilitate insertion of the locking device 28 through tissue. The tapered portion 56 is preferably sufficiently curved to facilitate movement of the tissue connector assembly 10 through connecting tissue in an anastomosis, for example. The tapered portion 56 may be formed from a metal alloy such as stainless steel or a suitable polymeric material and may be solid or in the form of a sleeve. Generally, portion 56 gradually diminishes in diameter to provide a smooth, non-stepped transition between the relatively small diameter of flexible member 18 to the larger diameter of locking device 28. The flexible member 18 may be swaged into the tapered portion 56, or a heat shrink plastic covering may hold the flexible member in place. The locking device 28 may also be curved.

The tubular member 50 is movable between a locked position (FIG. 4A) for holding the coil 26 in its compressed position and the wire 34 in its deformed position, and an unlocked position (FIG. 4C) for inserting or releasing the wire and coil. Three slots 58 are formed in the tubular member 50 extending from the proximal end 54 of the member and along at least a portion of the member (FIGS. 4B and 4C). The slots 58 are provided to allow the proximal end 54 of the tubular member 50 to open for insertion and removal of the wire 34 when the tubular member is in its unlocked position (FIG. 4C). It is to be understood that the number of slots 58 and configuration of the slots may vary, or the tubular member 50 may be formed to allow expansion of the proximal end 54 without the use of slots.

The proximal end 54 of the tubular member 50 includes a bore 62 having a diameter slightly greater than the outer diameter d of the wire 34, but smaller than the diameter of the enlarged portion 58 at the distal end of the wire and the outer diameter of the coil 26. The bore 62 extends into a cavity 64 sized for receiving the enlarged portion 38 of the wire 34. Member 50 may be described as having an annular flange 61 for releasably securing the enlarged portion 38. As shown in FIG. 4C, upon application of an inwardly directed radial squeezing force on the tubular member 50 the proximal end 54 of the tubular member is opened to allow for insertion or removal of the wire 34. When the force is released (FIG. 4A), the tubular member 50 moves back to its locked position and securely holds the wire 34 in place and compresses the coil 26. A disc 51 may be inserted into the tubular member 50 to act as a fulcrum and cause the proximal end 54 of the tubular member to open. Alternatively, the disc 51 may be integrally formed with the tubular member 50. As shown in FIG. 4A, the length l of the bore 62 or flange 61 determines the amount of compression of the coil, which in turn determines the amount of deformation of the wire 34. The greater the length l of the bore 62, the greater the compression of the coil 26 and the more straightening the wire 34 will undergo. The compression of the coil 26 is preferably limited so that the wire 34 is not stressed beyond its yield point. This allows the wire 34 to revert back to its original undeformed configuration and apply sufficient pressure to hold the connected tissue together.

It is to be understood that locking devices other than those described above may be used without departing from the scope of the invention. For example, a locking device (not shown) may comprise a tubular member having an opening formed in a sidewall thereof for receiving an end portion of the wire. The end of the wire may be bent so that it is biased to fit within the opening in the sidewall of the tubular member. An instrument, such as a needle holder may then be used to push the wire away from the opening in the tubular member and release the wire from the tubular member. Various other types of locking devices including a spring detent or bayonet type of device may also be used.

An alternate embodiment of the restraining device is shown in FIG. 5, and generally indicated with reference numeral 70. The restraining device 70 is used with a tubular (hollow) shape memory alloy wire 72 and comprises an elongated member (or mandrel) 74 sized for insertion into the wire or tube. The mandrel 74 is preferably formed from a material which is stiffer than the material of the wire 72 so that upon insertion of the mandrel into the wire, the wire is deformed into its open position. The restraining device 70 includes a stop 76 located at the proximal end of the wire 72. The stop operates to prevent the fastener from being pulled through the tissue, and limits axial movement of the mandrel 74 in the proximal direction (to the right as viewed in FIG. 5). The distal end of the mandrel 74 is attached to the suture 18 and includes a tapered portion 78. The tapered portion 78 may be a sleeve or may be solid and may be formed from any suitable metal or polymeric material, for example. It is to be understood that other types of restraining devices may be used without departing from the scope of the invention.

Another tissue connector assembly is shown in FIG. 6 and generally indicated with reference numeral 100. The tissue connector assembly 100 is the same as the first embodiment 10 except that a needle 102 is attached directly to a locking device 104 with the suture 18 of the first embodiment being eliminated. The tissue connector assembly 100 includes the needle 102, a restraining device 108, and a fastener 110. FIG. 6 shows the tissue connector assembly 100 with the fastener in its open (deformed) configuration. The fastener 110 may be the same as the fasteners 20, 40, 41, 43 described above and shown in FIGS. 3A-3G for the tissue connector assembly of the first embodiment, for example.

The restraining device 108 comprises a coil 112 and the locking device 104. The locking device 104 is similar to the locking device 28 shown in FIGS. 4A-4C, except that the distal end is configured for attachment directly to the needle 102. The needle 102 may be integrally formed with the locking device 104 or may be swaged, welded, threadably attached, or attached by any other suitable means to the locking device. The restraining device 70 shown in FIG. 5 may also be used with this embodiment 100 of the tissue connector assembly.

As noted above, the tissue connector assemblies 10, 100 have many uses. They may be especially useful for minimally invasive surgical procedures including creating an anastomosis between a vascular graft 12 and an artery 14 (FIGS. 2A-2G). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® (polyester fibers) or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

FIGS. 2A-2F show an exemplary use of the tissue connector assemblies 10, 100 for connecting a graft vessel 12 to an artery 14 (target vessel). In this example, two tissue connector assemblies 10 are used to make connections at generally opposite sides of the graft vessel and tissue connector assemblies 100 are used to make connections between those made with assemblies 10 (FIG. 6). The procedure may be accomplished with a beating heart procedure with the use of a heart stabilizer to keep the heart stable, for example. The procedure may also be performed endoscopically.

The patient is first prepped for standard cardiac surgery. After exposure and control of the artery 14, occlusion and reperfusion may be performed as required. After the arteriotomy of the snared graft vessel 12 has been made to the appropriate length, a tissue connector assembly 10 is attached to the free end of the graft vessel along an edge margin of the vessel. In order to attach the connector assembly 10, the surgeon grasps the needle 16 with a needle holder (e.g., surgical pliers, forceps, or any other suitable instrument) and inserts the needle 16 into the tissue of the graft vessel 12 in a direction from the exterior of the vessel to the interior of the vessel. The surgeon then releases the needle 16 and grasps a forward end of the needle which is now located inside the graft vessel 12 and pulls the needle and a portion of the suture 18 through the vessel. The needle 16 is passed through an opening 120 formed in the sidewall of the artery 14 and inserted into the tissue of the artery in a direction from the interior of the artery to the exterior of the artery. The surgeon then grasps the needle 16 located outside the artery 14 and pulls the needle and a portion of the suture 18 through the arterial wall. A second tissue connector assembly 10 may be inserted at a location generally 180 degrees from the location of the first tissue connector in a conventional "heel and toe" arrangement.

Figure 2A:
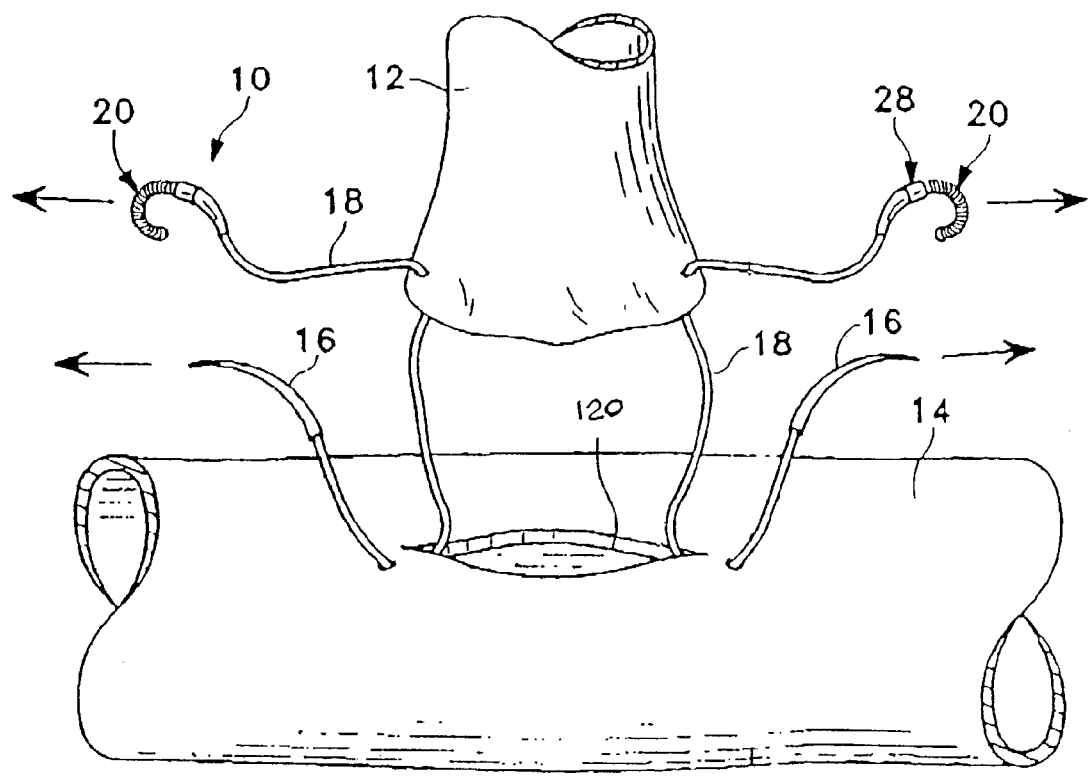
FIG. 2A shows two tissue connector assemblies of FIG. 1 in a first step for connecting a graft vessel to a target vessel.
Figure 2B:
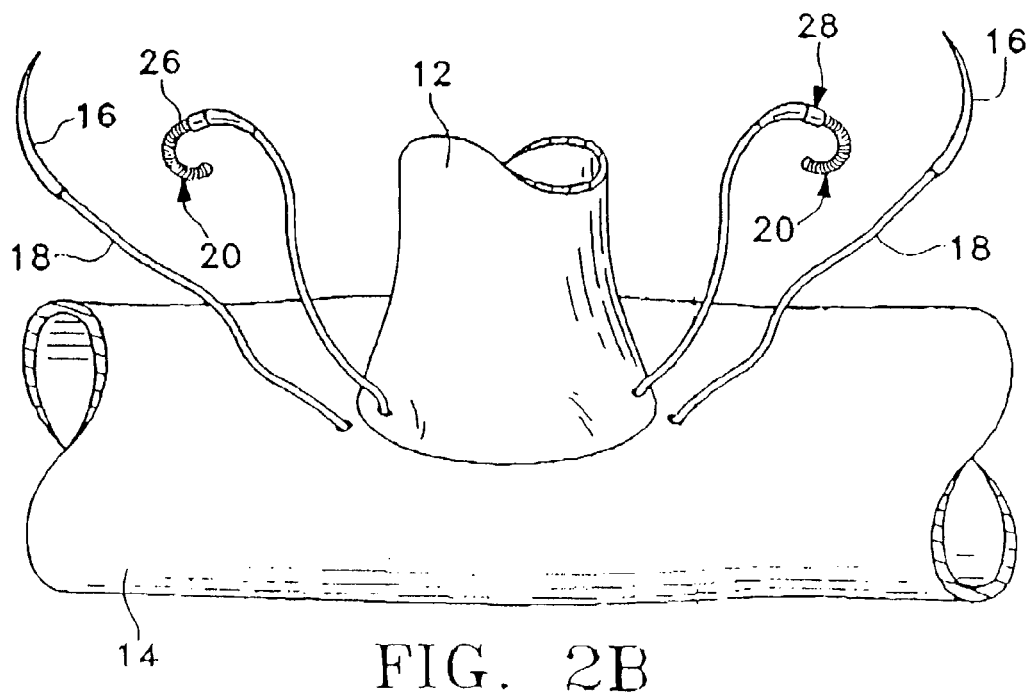
FIG. 2B shows a second step for connecting the graft vessel to the target vessel.
Figure 2C:
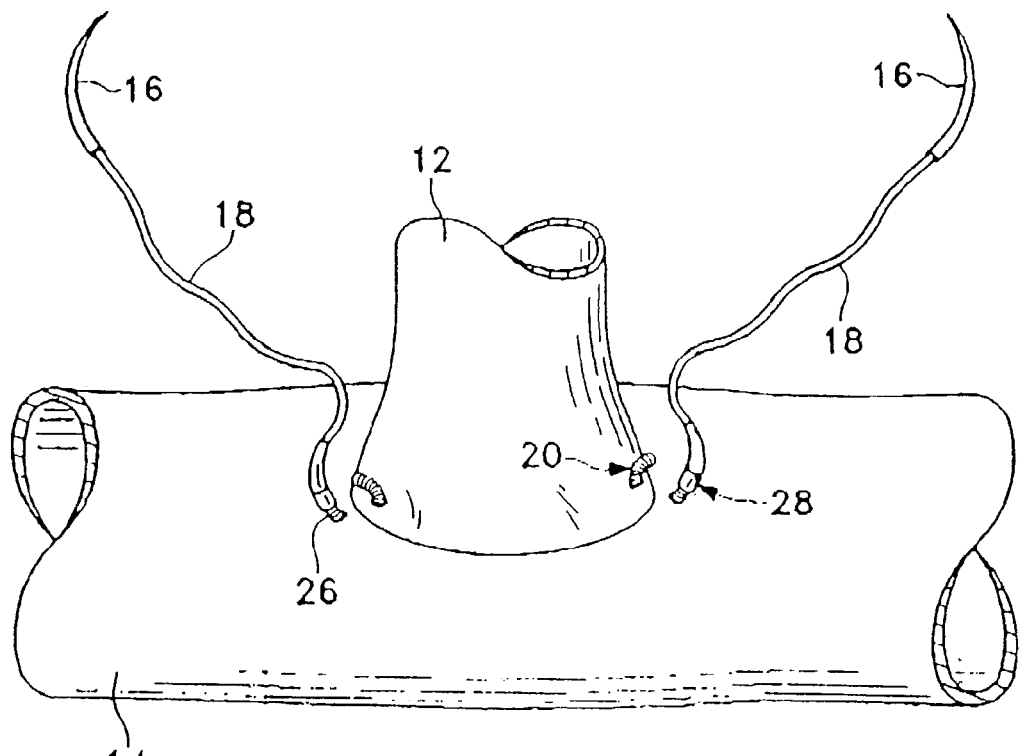
FIG. 2C shows a third step for connecting the graft vessel to the target vessel.
Figure 2D:
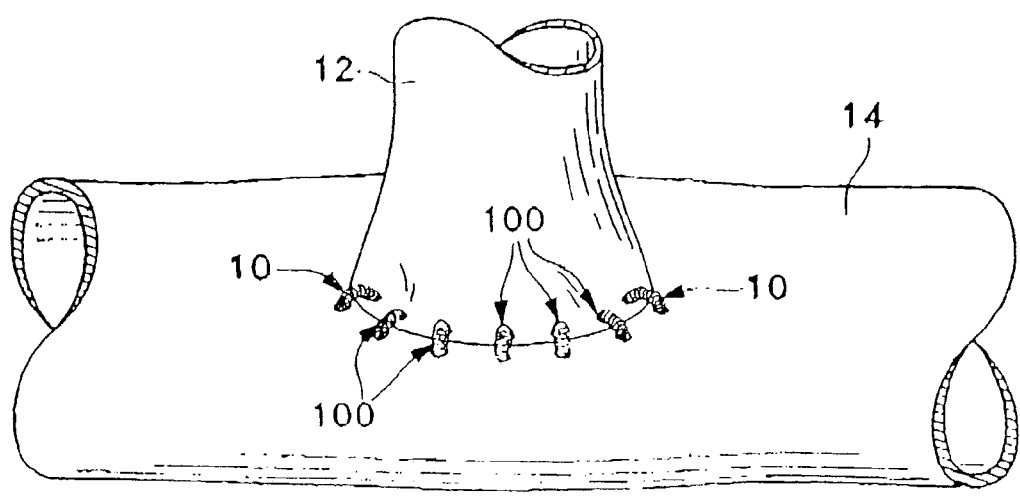
FIG. 2D shows the graft vessel connected to the target vessel.
Figure 2E:
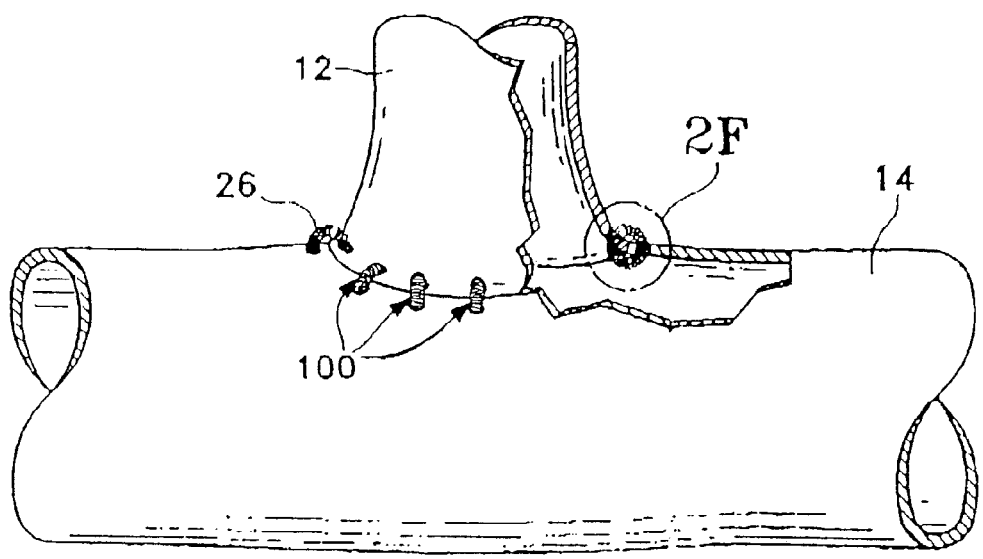
FIG. 2E is a front view of the connected graft and target vessels of FIG. 2D, with portions broken away to show detail.
Figure 2F:
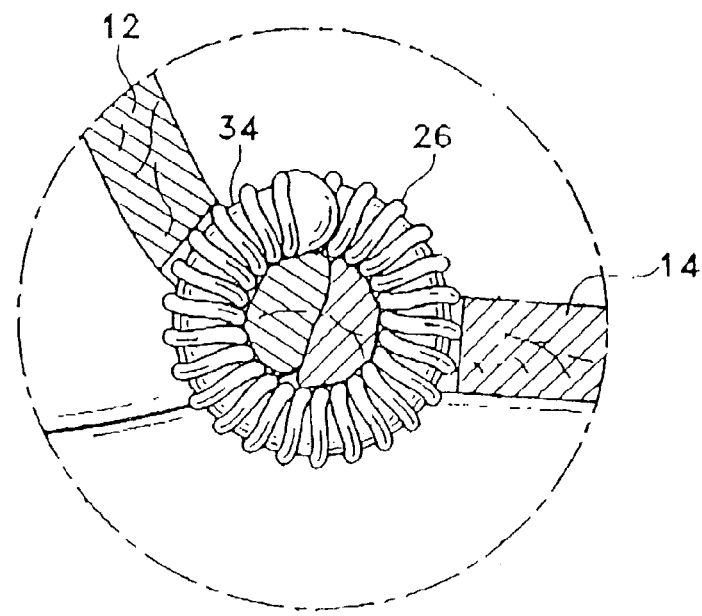
FIG. 2F is an enlarged view of the tissue connection shown in FIG. 2E.

Once the tissue connector assemblies 10 are inserted, the graft vessel 12 is positioned above and aligned with the opening 120 in the sidewall of the artery 14 (FIG. 2A). A section of each suture 18 is located between the graft vessel 12 and artery 14. The fasteners 20 and needles 16 are pulled generally away from the artery 14 to reduce the length of the suture 18 (eliminate slack of the suture) between the vessel 12 and artery and "parachute" the vessel onto the artery (FIG. 2B). The needles 16 are then pulled away from the artery 14 until each fastener 20 is positioned within the graft vessel 12 and artery with one end of each fastener 20 extending from the vessel and the opposite end of each fastener extending from the artery (FIG. 2C). The edges of the graft vessel 12 and artery 14 are positioned adjacent one another to form a continuous interior and exterior surface along the mating portions of the vessel and artery. As shown in FIG. 2F, the tissue is compressed within the fastener 20.

A surgical instrument (e.g., needle holder) is used to radially squeeze each locking device 28 to release the locking device from the fastener 20. Upon removal of the locking device 28, the coil 26 moves to its free uncompressed state which allows the wire 34 to return to its original undeformed closed position (FIG. 2D). As the wires 34 move to their closed position the adjacent tissues of the graft vessel 12 and artery 14 which were previously pulled together during the parachuting of the graft vessel onto the artery, are squeezed together to securely engage the graft vessel and artery (FIGS. 2E and 2F). It should be noted that as the locking device 28 is squeezed two steps are accomplished. The fastener 20 is released from the locking device 28, thus allowing the coil 26 to uncompress and the wire 34 to move to its closed configuration, and the needle 16 is released from the fastener. Thus, in this embodiment, the locking device 28 provides for simultaneous actuating closure of the fastener 20 and release of the needle 16 from the fastener.

The tissue connector assemblies 100 are subsequently inserted at circumferentially spaced locations around the periphery of the graft vessel to sealingly fasten the graft vessel 12 to the artery 14. The needle 102 of the fastener 100 is inserted into the graft vessel 12 from the exterior surface of the graft vessel and pushed through the graft vessel and artery 14 tissue. The needle holder is then used to pull the needle 102 through the arterial wall. An instrument (same needle holder or other suitable instrument) is used to apply a squeezing force to the locking device 104 to release the wire and coil 112 from the needle 102. This allows the coil 112 to move to its uncompressed configuration and the wire to move to its closed position. It should be noted that the tissue connector assemblies 10 may remain in their open position while the tissue connector assemblies 100 are inserted into the tissue and moved to their closed position. The locking devices 28 of the tissue connector assemblies 10 may subsequently be removed from the fasteners 20 to allow the fasteners to move to their closed position. The number and combination of tissue connectors assemblies 10, 100 required to sealingly secure the connecting tissues together may vary. For example, only tissue connector assemblies 10 may be used to complete the entire anastomosis.

Although the coil 26 is shown remaining on the wire (FIG. 2D), it is to be understood that the coil 26 may also be removed from the wire 34, leaving only the wire in the connected tissue.

As an alternative to inserting tissue connector assemblies 10 at "heel and toe" locations described above, a number of tissue connectors 10 may be inserted generally around the location of the heel. The graft vessel may then be pulled towards the artery to determine whether the opening formed in the sidewall of the artery is large enough before completing the anastomosis.

Figure 2G:
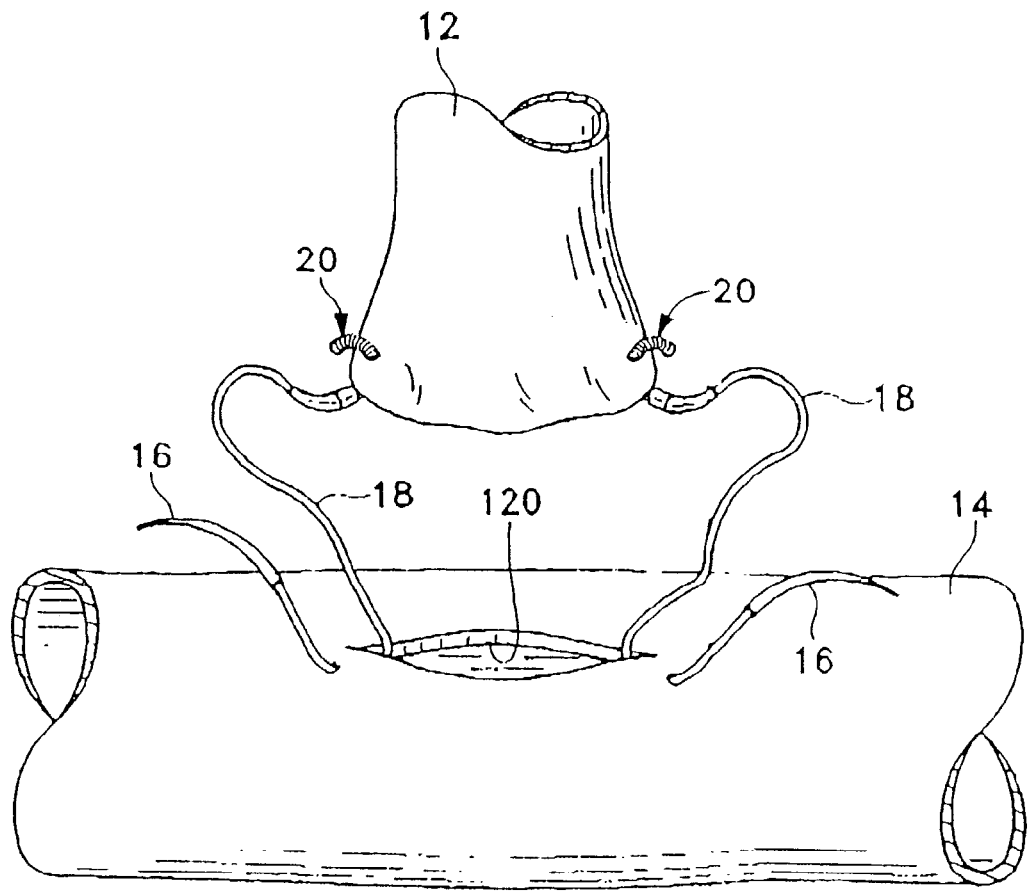
FIG. 2G shows an alternate method for connecting the graft vessel to the target vessel with the tissue connector assembly of FIG. 1.

The graft vessel 12 may also be parachuted onto the artery 14 in the method shown in FIG. 2G. The needle is inserted into the graft vessel 12 and artery 14 as described above and the suture 18 is pulled through the vessel so that the fastener 20 is positioned within the vessel and artery. The needles 16 are then pulled away from the artery 14 to "parachute" the graft vessel 12 onto the artery. The anastomosis may then be completed as described above.

Although the suturing procedure has been described for an end-to-side anastomosis, it should be appreciated that the procedure is applicable to an end-to-end and side-to-side anastomosis, connecting various tissue structures including single and multiple tissue structures, and puncture sites, and connecting tissue to a prosthetic graft or valve, for example.

It will be observed from the foregoing that the tissue connector assemblies of the present invention have numerous advantages. Importantly, the assemblies are easier and faster to apply than conventional sutures which require tying multiple knots. The assemblies also may be used in minimally invasive procedures including endoscopic procedures.

All references cited above are incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A method for connecting portions of material, at least one portion comprising tissue, the method comprising:
   drawing multiple portions of material, at least one of which comprises tissue, together with a tissue connector assembly having a clip restrained in an open position with a restraint in a biased state, said restraint configured to define differing, biased and released states apart from said clip; and
   releasing the restraint from said biased state to said released state to allow said clip to move toward a closed, loop-shaped configuration and secure said material portions therein,
   wherein said tissue connector assembly is pulled with at least a portion of said clip positioned through one of said portions of material.

2. The method of claim 1 wherein said portions of material are drawn together by pulling said tissue connector assembly.

3. The method of claim 2 wherein said tissue connector assembly is pulled with at least a portion of said tissue connector assembly positioned in said portions of material.

4. The method of claim 1 including inserting a flexible member coupled to said clip through said portions of material, and at least one end of said tissue connector assembly is pulled to draw said materials together.

5. The method of claim 4 wherein said clip is pulled to draw said portions of material together.

6. The method of claim 1 wherein said tissue connector assembly is inserted into said multiple portions of material with a needle.

7. The method of claim 6 including simultaneously actuating closure of said clip and release of said needle therefrom.

8. The method of claim 6 including manipulating a portion of said tissue connector assembly to both actuate closure of said clip and release said needle from said clip.

9. The method of claim 6 wherein said restraint releasably couples the clip to said needle.

10. The method of claim 6 wherein said restraint releasably couples the clip to said needle through a suture.

11. The method of claim 1 wherein the closed, loop-shaped configuration is memory set.

12. A method for connecting portions of material, at least one portion comprising tissue, the method comprising:
    drawing multiple portions of material, at least one of which comprises tissue, together with a tissue connector assembly including a clip, which has an open position and a memory set closed, loop-shaped configuration, a needle, which has a tissue piercing end; and
    a restraining device that holds the clip in the open configuration and releasably couples the clip to the needle through a suture; and
    releasing the restraining device to allow the clip to move toward said closed configuration.

13. The method of claim 12 wherein releasing the restraining device comprises manipulating the restraining device to allow the clip to move toward the closed configuration and to release the needle from the clip.

14. The method of claim 12 including simultaneously actuating closure of said clip and release of said needle therefrom.

15. A method for connecting portions of material, at least one portion comprising tissue, the method comprising:
    drawing multiple portions of material, at least one of which comprises tissue, together with a tissue connector assembly having a clip restrained in an open position with a restraint including a locking mechanism, wherein said tissue connector assembly is inserted into said multiple portions of material with a needle;
    releasing said locking mechanism, wherein releasing of said locking mechanism simultaneously releases said needle from said clip and transitions said restraint in a manner allowing said clip to move toward a closed, loop-shaped configuration and secure said material portions therein.

16. The method of claim 15 wherein said restraint releasably couples the clip to said needle.

17. The method of claim 15 wherein said restraint releasably couples the clip to said needle through a suture.

18. The method of claim 15 wherein said tissue connector assembly is pulled with at least a portion of said clip positioned through one of said portions of material.

19. A method for connecting portions of material, at least one portion comprising tissue, the method comprising:
    drawing multiple portions of material, at least one of which comprises tissue, together with a tissue connector assembly having a clip restrained in an open position with a restraint;
    lessening a bias applied on said clip by said restraint to allow said clip to move toward a closed, loop-shaped configuration and secure said material portions therein;
    wherein said tissue connector assembly is inserted into said multiple portions of material with a needle; and
    manipulating a portion of said tissue connector assembly adjacent said needle to both lessen the bias applied by said restraint and release said needle from said clip.

20. The method of claim 19 wherein said restraint releasably couples the clip to said needle.

21. The method of claim 19 wherein said restraint releasably couples the clip to said needle through a suture.

22. The method of claim 19 wherein said tissue connector assembly is pulled with at least a portion of said clip positioned through one of said portions of material.

* * * * *